(12) United States Patent
Underwood et al.

(10) Patent No.: US 9,585,788 B2
(45) Date of Patent: Mar. 7, 2017

(54) VITRECTOMY PROBE WITH ADJUSTABLE CUTTER PORT SIZE

(75) Inventors: John R. Underwood, Laguna Nigel, CA (US); Matthew Braden Flowers, Lake Forest, CA (US); Jack Robert Auld, Laguna Niguel, CA (US); John Christopher Huculak, Mission Viejo, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/591,336

(22) Filed: Aug. 22, 2012

(65) Prior Publication Data

US 2013/0158584 A1 Jun. 20, 2013

Related U.S. Application Data

(63) Continuation of application No. 13/419,061, filed on Mar. 13, 2012, now Pat. No. 9,517,161.

(60) Provisional application No. 61/577,989, filed on Dec. 20, 2011.

(51) Int. Cl.
*A61B 17/32* (2006.01)
*A61F 9/007* (2006.01)
*A61B 17/00* (2006.01)

(52) U.S. Cl.
CPC *A61F 9/00763* (2013.01); *A61B 2017/00544* (2013.01)

(58) Field of Classification Search
CPC .................. A61F 9/00763; A61B 2017/00544
USPC .................................. 606/166, 170, 171, 172
See application file for complete search history.

(56) References Cited

U.S. PATENT DOCUMENTS

| | | | |
|---|---|---|---|
| 2,196,927 A | 4/1940 | Larson | |
| 2,564,445 A | 8/1951 | Parsons | |
| 3,569,753 A | 3/1971 | Babikyan | |
| 3,884,238 A | 5/1975 | O'Malley et al. | |
| 4,005,734 A | 2/1977 | Kubik | |
| 4,210,146 A | 7/1980 | Banko | |
| 4,481,768 A | 11/1984 | Goshorn et al. | |
| 4,489,724 A | 12/1984 | Arnegger | |
| 4,548,205 A | 10/1985 | Armeniades | |
| 4,589,414 A | 5/1986 | Yoshida et al. | |
| 4,768,506 A | 9/1988 | Parker et al. | |
| 4,909,249 A | 3/1990 | Akkas et al. | |
| 4,940,468 A * | 7/1990 | Petillo | 606/170 |
| 4,986,827 A | 1/1991 | Akkas et al. | |
| 4,989,614 A | 2/1991 | Dejter et al. | |
| 5,019,035 A * | 5/1991 | Missirlian | A61F 9/00763 604/22 |

(Continued)

OTHER PUBLICATIONS

International Search Report and Written Opinion of the International Searching Authority, International Application No. PCT/2011/062797, dated Mar. 9, 2012, 10 pages.

(Continued)

*Primary Examiner* — Gregory Anderson
*Assistant Examiner* — Sarah Simpson
(74) *Attorney, Agent, or Firm* — Darien Reddick

(57) ABSTRACT

Vitrectomy probes and system related thereto are disclosed herein. The disclosure describes various example vitrectomy probes having an adjustable cutting port size. Various example features are described for adjusting the size of the cutting port. Further, the disclosure provides examples for adjusting the size of the cutter port while the vitrectomy probe is in operation.

12 Claims, 22 Drawing Sheets

(56) References Cited

U.S. PATENT DOCUMENTS

| | | |
|---|---|---|
| 5,020,535 A | 6/1991 | Parker et al. |
| 5,047,008 A | 9/1991 | De Juan, Jr. et al. |
| 5,059,204 A | 10/1991 | Lawson et al. |
| 5,314,440 A | 5/1994 | Shapiro |
| 5,350,355 A | 9/1994 | Sklar |
| 5,547,473 A | 8/1996 | Peyman |
| 5,562,691 A | 10/1996 | Tano et al. |
| 5,626,595 A | 5/1997 | Sklar et al. |
| 5,632,758 A | 5/1997 | Sklar |
| 5,649,547 A | 7/1997 | Ritchart et al. |
| 5,669,923 A | 9/1997 | Gordon |
| 5,722,980 A | 3/1998 | Schulz et al. |
| 5,759,153 A | 6/1998 | Webler et al. |
| 5,843,111 A | 12/1998 | Vijfvinkel |
| 5,910,110 A | 6/1999 | Bastable |
| 6,010,496 A | 1/2000 | Appelbaum et al. |
| 6,165,136 A | 12/2000 | Nishtala |
| 6,176,865 B1 | 1/2001 | Mauze et al. |
| 6,261,241 B1 | 7/2001 | Burbank et al. |
| 6,485,499 B1 | 11/2002 | Oberkamp et al. |
| 6,514,268 B2 | 2/2003 | Finlay et al. |
| 6,527,736 B1 | 3/2003 | Attinger et al. |
| 6,629,986 B1 | 10/2003 | Ross et al. |
| 6,689,071 B2 | 2/2004 | Burbank et al. |
| 6,773,445 B2 | 8/2004 | Finlay et al. |
| 7,025,732 B2 | 4/2006 | Thompson et al. |
| 7,517,322 B2 | 4/2009 | Weikel, Jr. et al. |
| 7,717,861 B2 | 5/2010 | Weikel et al. |
| 7,785,321 B2 | 8/2010 | Baerveldt |
| 8,038,692 B2 | 10/2011 | Valencia et al. |
| 8,187,293 B2 | 5/2012 | Kirchhevel |
| 2002/0026869 A1 | 3/2002 | Morita et al. |
| 2002/0124893 A1 | 9/2002 | Frank et al. |
| 2002/0173814 A1 | 11/2002 | Jung et al. |
| 2003/0078609 A1 | 4/2003 | Finlay et al. |
| 2003/0145721 A1 | 8/2003 | Oka et al. |
| 2003/0159738 A1 | 8/2003 | Lee |
| 2004/0049217 A1 | 3/2004 | Ross et al. |
| 2004/0138687 A1 | 7/2004 | Himes |
| 2004/0204732 A1 | 10/2004 | Muchnik |
| 2004/0211476 A1 | 10/2004 | Hager |
| 2005/0065453 A1 | 3/2005 | Shabaz et al. |
| 2005/0080441 A1 | 4/2005 | Dodge et al. |
| 2006/0167377 A1 | 7/2006 | Ritchart et al. |
| 2006/0167378 A1 | 7/2006 | Miller |
| 2006/0200040 A1 | 9/2006 | Weikel, Jr. et al. |
| 2007/0135752 A1 | 6/2007 | Domash et al. |
| 2007/0185512 A1 | 8/2007 | Kirchhevel |
| 2007/0185514 A1 | 8/2007 | Kirchhevel |
| 2008/0114264 A1 | 5/2008 | Weikel, Jr. et al. |
| 2008/0168985 A1 | 7/2008 | Turner et al. |
| 2008/0172078 A1 | 7/2008 | Svetic |
| 2009/0048533 A1 | 2/2009 | Miller |
| 2009/0157111 A1 | 6/2009 | Goh et al. |
| 2010/0030108 A1 | 2/2010 | Anderson et al. |
| 2010/0145374 A1 | 6/2010 | Perkins |
| 2010/0286691 A1 | 11/2010 | Kerr et al. |
| 2010/0317998 A1* | 12/2010 | Hibner et al. ............. 600/567 |
| 2011/0054349 A1 | 3/2011 | Hibner |
| 2011/0295293 A1 | 12/2011 | Agahi |
| 2012/0116391 A1 | 5/2012 | Houser et al. |
| 2012/0157906 A1 | 6/2012 | Underwood et al. |
| 2012/0158029 A1 | 6/2012 | Underwood et al. |
| 2013/0144317 A1 | 6/2013 | Valencia |

OTHER PUBLICATIONS

International Search Report for PCT/US2012/069216, dated Feb. 26, 2013, 2 pages.

International Preliminary Report on Patentability and Written Opinion of the International Searching Authority, International Application No. PCT/2011/062797, dated Mar. 9, 2012, 9 pages.

International Preliminary Report Patentability and Written Opinion of the International Searching Authority, International Application No. PCT/2012/069216, dated Jun. 24, 2014, 11 pages.

Brushless DC Motor, http://www.allaboutcircuits.com/vol_2/chpt_13/6.html, Dec. 18, 2010, retrieved using the "Internet Wayback Machine," 3 pages, vol. 2, Chapter 13. Last accessed Jun. 27, 2014.

Supplemental European Search Report for Application No. 11851826.5, Publication No. 2648630, Published Oct. 16, 2013, 8 pages.

Supplemental European Search Report for Application No. EP12860860.1, Publication No. EP2793717, Published Oct. 29, 2014, 6 pages.

* cited by examiner

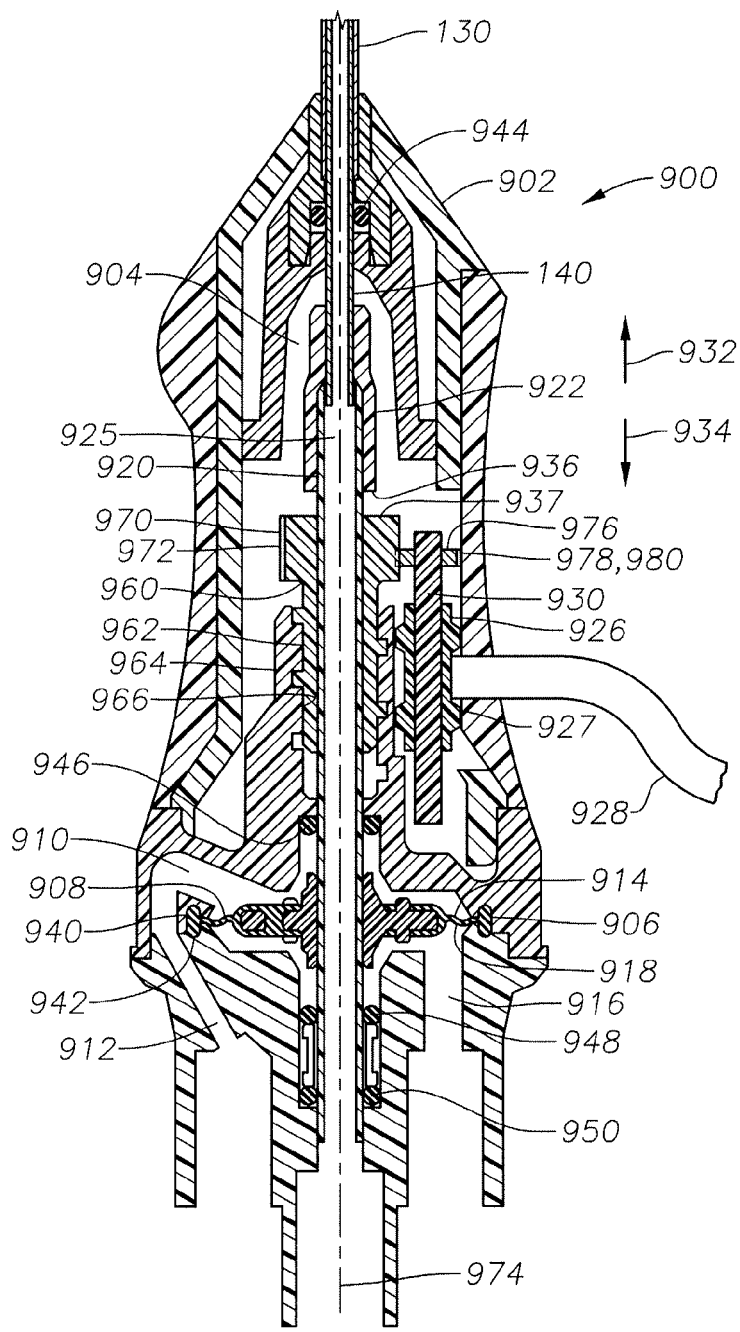
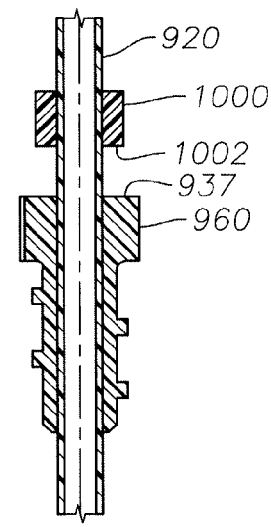
Fig. 9
Fig. 10

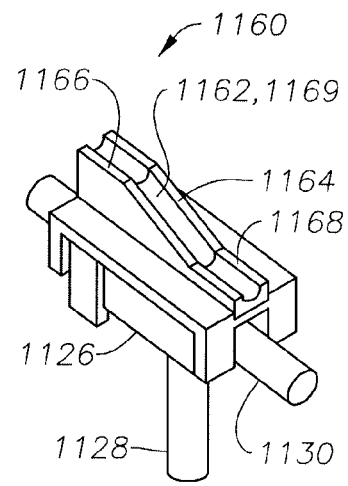
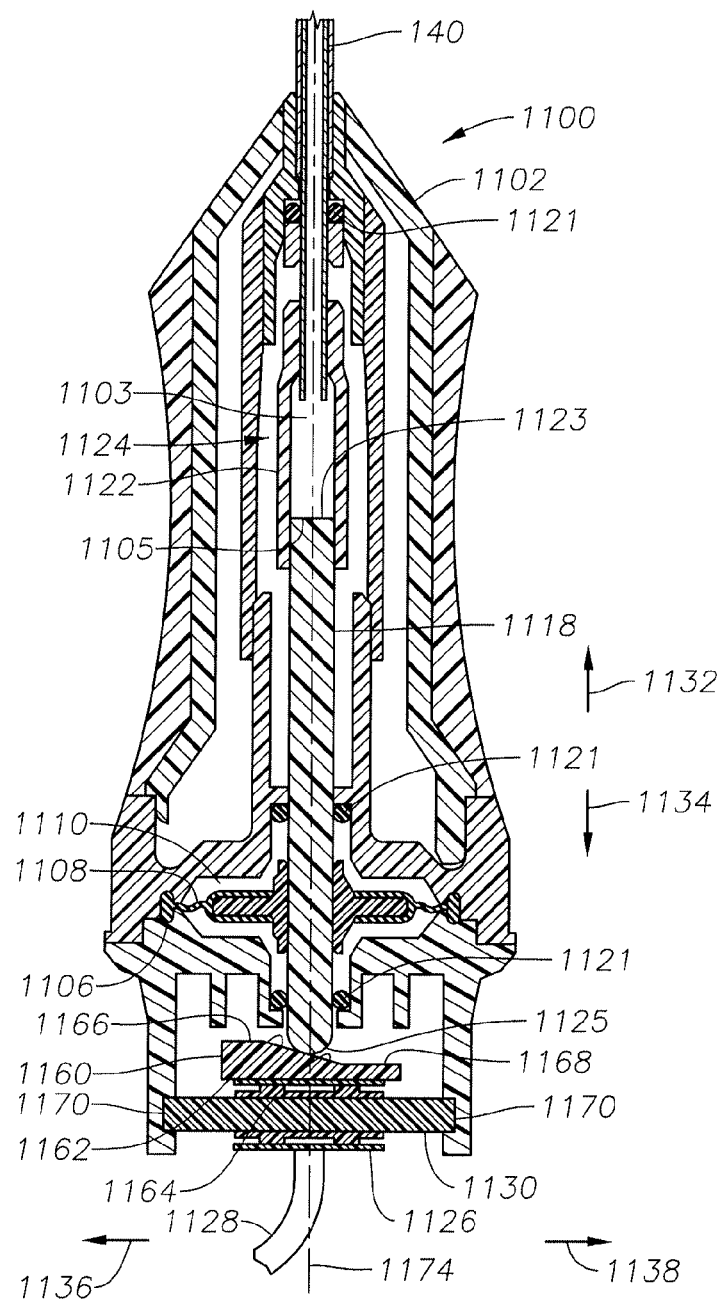
Fig. 13
Fig. 12

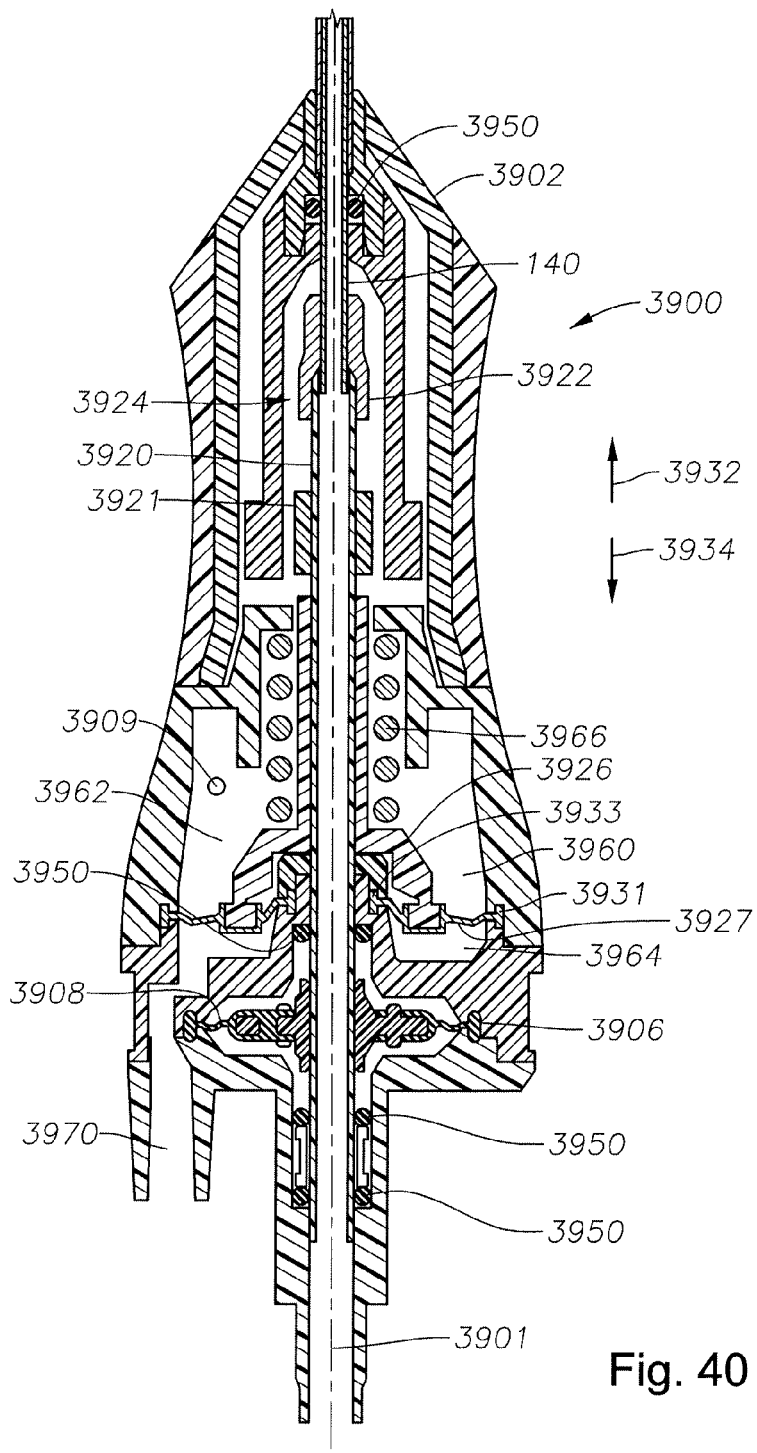
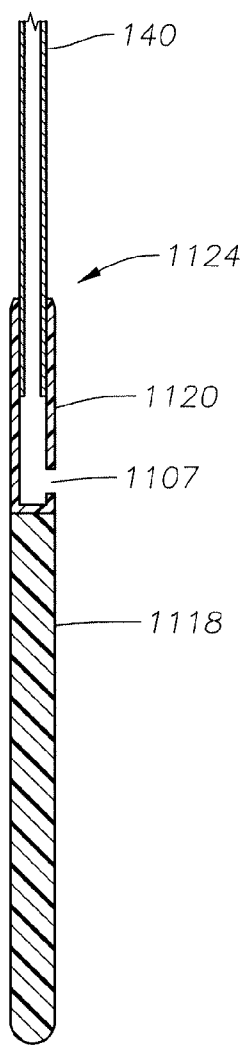
Fig. 40
Fig. 41

VITRECTOMY PROBE WITH ADJUSTABLE CUTTER PORT SIZE

CROSS REFERENCE TO RELATED APPLICATIONS

This application is a continuation application of prior application Ser. No. 13/419,061, filed Mar. 13, 2012, which claims the benefit of U.S. Provisional Application No. 61/577,989, filed Dec. 20, 2011, the contents of which are incorporated herein by reference. This application also relates to application Ser. No. 13/419,212, filed Mar. 13, 2012 now U.S. Pat. No. 9,517,161; Application Ser. No. 13/419,167, filed Mar. 13, 2012; application Ser. No. 13/469,391, filed May 11, 2012; Application Ser. No. 13/469,435, filed May 11, 2012; and application Ser. No. 13/591,331, filed Aug. 22, 2012.

TECHNICAL FIELD

The present disclosure relates to an ophthalmic microsurgical instrument. Particularly, the present disclosure is directed to a vitreoretinal surgical instrument, e.g., a vitrectomy probe, having a user-selectable cutter port size.

BACKGROUND

Vitrectomy probes are used during vitreoretinal surgery to remove ocular tissues, such as vitreous humor and membranes covering the retina. These probes have a port for drawing in and dissecting tissues. The port opens a fixed amount, tissue is drawn into the port, the port closes, severing the tissue, and the tissue is aspirated. This action may be repeated to remove desired tissues.

SUMMARY

According to one aspect, the disclosure describes a vitrectomy probe that may include a housing, a cutter from a first end of the housing along a longitudinal axis, an oscillator operable to reciprocate an interior assembly, and a stroke limiter operable to limit the size of the adjustable port. The cutter may include an outer cutting member coupled to the housing and the interior assembly. The interior assembly may include an inner cutting member slideable within the outer cutting member. The interior assembly may be slideable between a retracted position and an extended position. The cutter may also include an adjustable port. A size of the adjustable port may be defined by an edge of an opening formed in the outer cutting member and an end surface of the inner cutting member when the inner cutting member is in a fully retracted position. The stroke limiter may include a motor operably coupled to the stroke limiter and operable to displace the stroke limiter along the longitudinal axis.

The motor may include a rotatable shaft and a coupler coupled to the shaft and the stroke limiter. The motor may be operable to rotate the stroke limiter about the longitudinal axis. The stroke limiter may include a first threaded exterior surface, and a portion of the housing may include a second threaded surface. The first threaded surface matingly engages the second threaded surface. A bore may be formed in the housing. The second threaded surface may be formed on an interior surface of the bore. A rotation of the motor in a first direction displaces the stroke limiter in a first direction along the longitudinal axis, and a rotation of the motor in a second direction displaces the stroke limiter in a second direction along the longitudinal axis. Displacement of the stroke limiter in the first direction along the longitudinal direction may extend the stroke limiter towards the inner cutting member, and displacement of the stroke limiter in the second direction along the longitudinal direction may retract the stroke limiter from the inner cutting member. The interior assembly may also include an extension extending through the oscillator and be coupled to the inner cutting member. A location where the stroke limiter contacts the extension may define the fully retracted position. A passage may extend through the interior assembly.

The details of one or more implementations of the present disclosure are set forth in the accompanying drawings and the description below. Other features, objects, and advantages will be apparent from the description and drawings, and from the claims.

DESCRIPTION OF DRAWINGS

FIG. 9 shows a cross-sectional view of an example vitrectomy probe having a user-controllable cutter port size adjustable with a piezoelectric motor.

FIG. 10 shows a cross-sectional detail view of a portion of the example vitrectomy probe of FIG. 9.

FIG. 12 shows a cross-sectional view of the example vitrectomy probe shown in FIG. 11 taken along a plane that is 90 offset from the view shown in FIG. 11 about a centerline of the vitrectomy probe.

FIG. 13 is a perspective view of an example stroke limiter of the example vitrectomy probe of FIGS. 11 and 12.

FIGS. 39 and 40 show another example vitrectomy probe having an adjustable cutter port size.

FIG. 41 shows an example interior assembly that may be utilized with one or more of the example probes described herein.

DETAILED DISCLOSURE

The present disclose describes microsurgical instruments including a variable-sized port for removing tissues. Particularly, the present disclosure describes ophthalmic vitrectomy probes with a user-selectable, variable-sized port used, for example, in posterior segment ophthalmic surgeries. A medical practitioner, such as a surgeon, can control the probe's port size to maximize cutting efficiency and tissue flowability. Alteration of the port size may be accomplished in numerous ways. For example, the port size may be adjusted fluidically (e.g., pneumatically or hydraulically), mechanically, electrically, manually, or by a combination of any of these. Some implementations may utilize a mechanical stop to control a size of the port opening. In other implementations, a size of the port opening may be controlled fluidically. While the examples set out below are described with respect to ophthalmic surgical procedures, the disclosure is not so limited. Rather, the examples provided are merely that, and the scope of the disclosure may be applicable to any surgical instrument for which a variable sized port may be desirable or to which a variable-sized port may be adapted. Further, fluidic actuation of aspects of the probes described herein (e.g., a portion of a probe cutter or stroke limiter) are described herein as being pneumatic. However, such a description is provided as an example only. Thus, it is understood that such a description encompasses hydraulic actuation as well.

Figure 1:
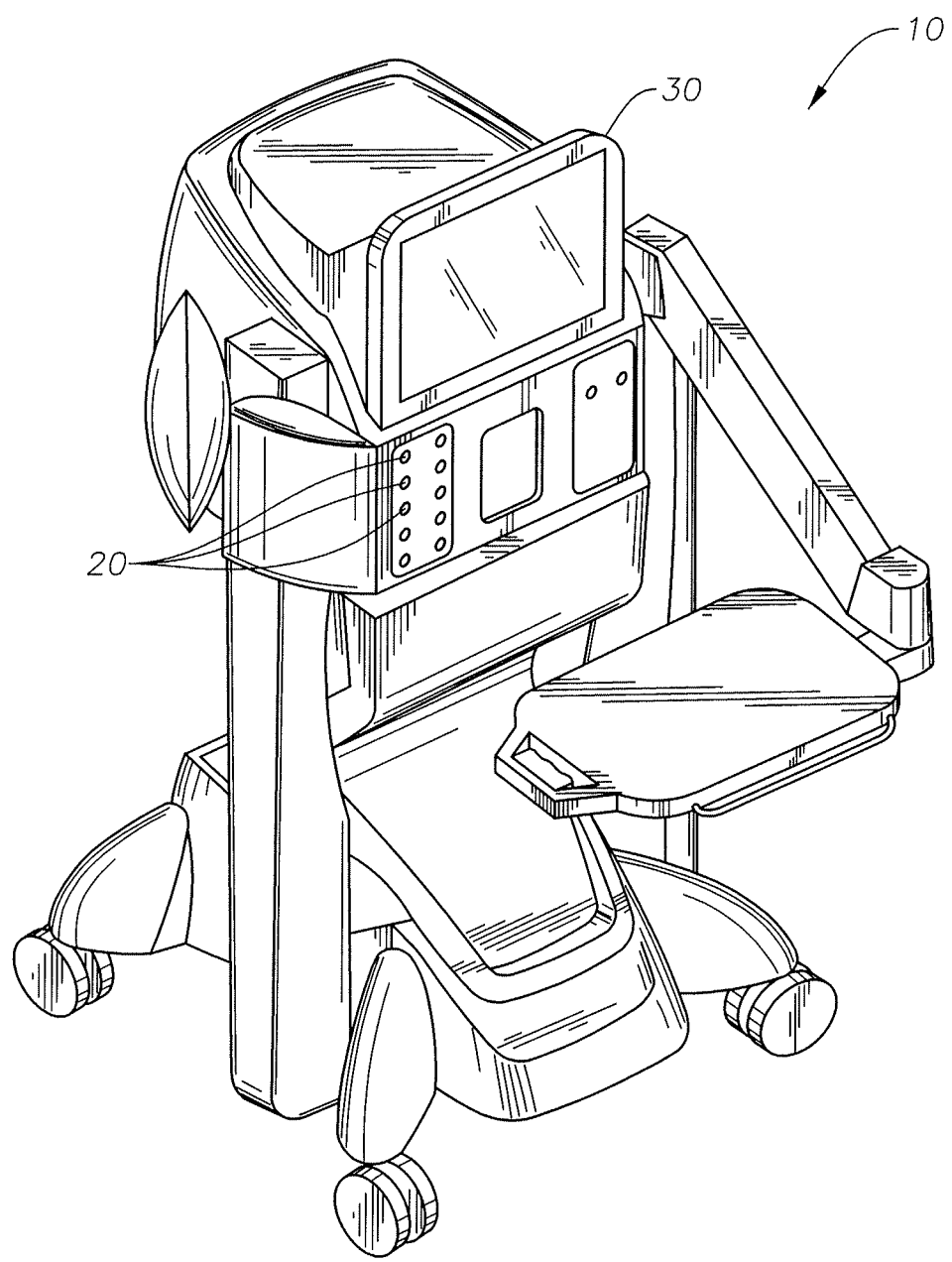
FIG. 1 shows an example surgical console.

FIG. 1 shows an example surgical console (interchangeably referred to as "console") 10 within the scope of the present disclosure. The surgical console may be a vitreoretinal surgical console, such as the Constellation® surgical console produced by Alcon Laboratories, Inc., 6201 South Freeway, Fort Worth, Tex. 76134 U.S.A. The console 10 may include one or more ports 20. One or more of the ports 20 may be utilized, for example, to provide infusion and/or irrigation fluids to the eye or to aspirate materials from the eye. The console 10 may also include a display 30 for interfacing with the console 10, such as to establish or change one or more operations of the console 10. In some instances, the display 30 may include a touch-sensitive screen for interacting with the console 10 by touching the screen of the display 30. A probe, such as a vitrectomy probe, may be coupled to a port 20 for dissecting ocular tissues and aspirating the ocular tissues from the eye.

Figure 2:
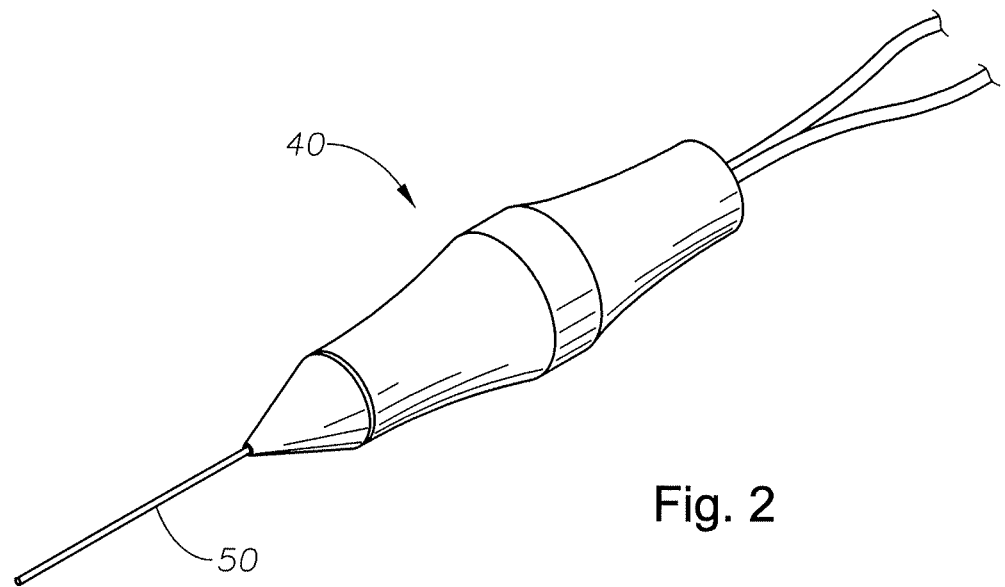
FIG. 2 shows an example vitrectomy probe having a cutter with an adjustable-sized cutting port.
Figure 3:
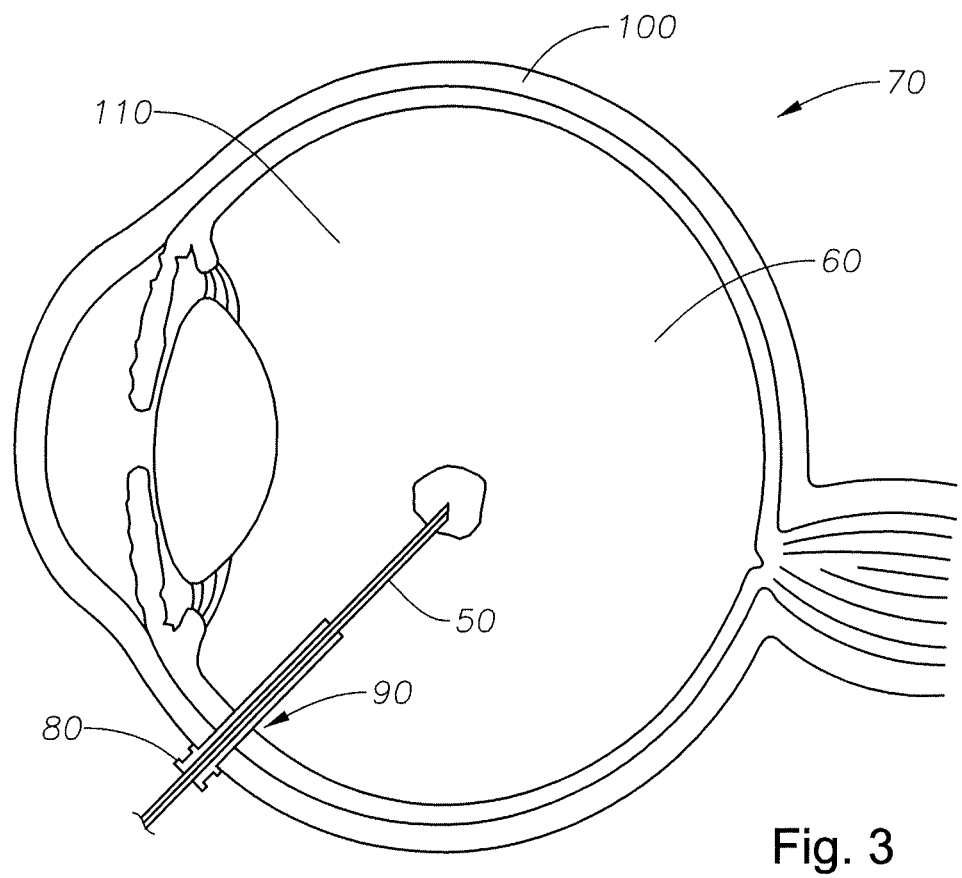
FIG. 3 shows a cross-sectional view of an eye in which a cutter of a vitrectomy probe extends into a posterior segment of the eye.

FIG. 2 shows an example vitrectomy probe 40. The probe 40 includes a cutter 50. As illustrated in FIG. 3, during an ophthalmic surgical procedure, such as a retinal surgical procedure, the cutter 50 may be inserted into the posterior segment 60 of the eye 70, such as through a cannula 80 disposed in an incision 90 through the sclera 100 of the eye 70, to remove and aspirate ocular tissues. For example, during a retinal surgical procedure, the cutter 50 may be inserted into the posterior chamber 60 of the eye 70 to remove vitreous humor (interchangeably referred to as "vitreous") 110, a jelly-like substance that occupies the volume defined by the posterior segment 60. The cutter 50 may also be used to remove membranes covering the retina or other tissues.

FIGS. 4-8 show detailed, cross-sectional views of an example cutter 50 with ports 120 adjusted to various sizes. The example cutter 50 may include a hollow outer cutting member 130. The outer cutting member 130 includes an opening 115. The cutter 50 may also include a hollow inner cutting member 140 coaxially arranged within the outer cutting member 130 and slideable therein. The inner cutting member 140 may also include a cutting edge 150. The cutting edge 150 and the opening 115 may define the port 120. Thus, for example, a position of the cutting edge 150 relative to the opening 115 may define the size of the port 120. The size of the port 120 may be varied by, for example, the fully retracted position of the inner cutting member 140.

In operation, tissue may enter into the cutter 50 through the port 120 and be dissected by the cutting edge 150 as the inner cutting member 140 is reciprocated within the outer cutting member 130. The tissue may be dissected by the cutting edge 150 as the inner cutting member 140 extends within the outer cutting member 130, closing the opening 115 (see, e.g., FIG. 8). A vacuum may also be generated within an interior channel 160 of the cutter 50 to aspirate the dissected tissue.

In some implementations, the inner cutting member 140 is reciprocated within the outer cutting member 130 pneumatically. However, the disclosure is not so limited. Rather, the cutter 50 may be operated in other ways. For example, the cutter 50 may be operated electrically, hydraulically, or in any number of other ways. Therefore, the description of utilizing pneumatics to operate the cutter 50 in one or more of the implementations is provided merely as an example and is not intended to be limiting.

Figure 4:
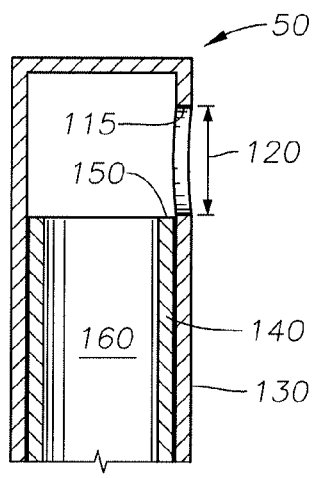
FIGS. 4-8 are detailed cross-sectional views of a vitrectomy cutter showing cutter ports with different sizes.
Figure 5:
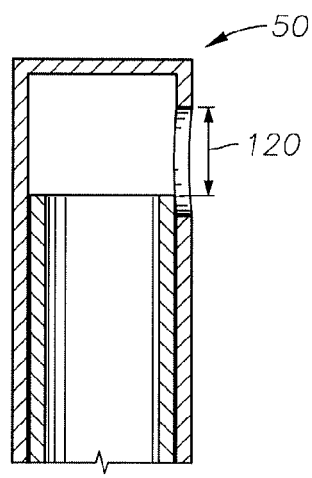
Figure 6:
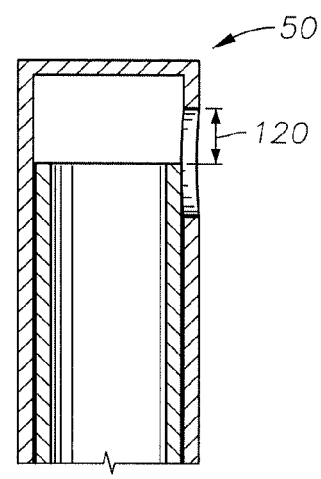
Figure 7:
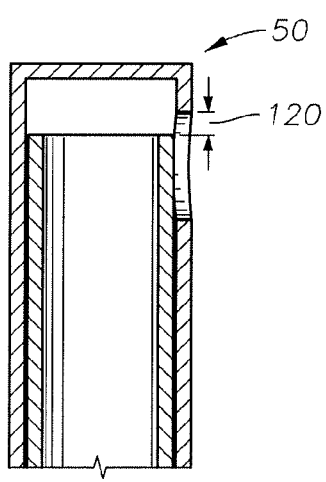
Figure 8:
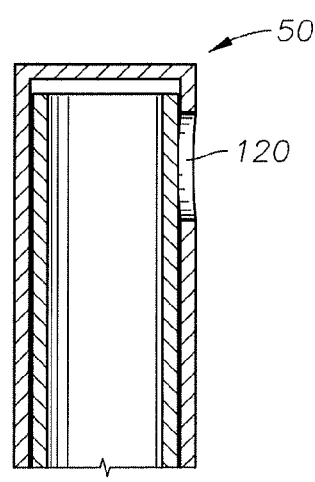

During an ophthalmic surgical procedure, it may be desirable to change a size of the port 120. For example, a port size may be changed to maximize cutting efficiency and tissue flowability. Further, a cutter having an adjustable port size provides for altering, for example, a duty cycle, cut rate, and port opening independent of each other. FIGS. 4-8 illustrate a cutter 50 having port 120 adjusted to different sizes. For example, FIG. 4 shows the size of port 120 adjusted to 100 percent; FIG. 5 shows the size of port 120 at approximately 75 percent; FIG. 6 shows the size of port 120 at approximately 50 percent; and FIG. 7 shows the size of port 120 at approximately 25 percent. FIG. 8 shows the port 120 in a closed configuration. While FIGS. 4-8 show port sizes at 75%, 50%, 25%, and closed are described, these port sizes are not intended to be limiting. Rather, it is within the scope of the disclosure that the port size of a probe may be adjusted to any desired size.

In some implementations, the probe may include a piezoelectric linear motor to alter the port size. FIG. 9 shows a partial cross-sectional view of an example probe 900. The probe 900 may include a housing 902 defining an interior chamber 904, and an oscillator or motor 906. The outer cutting member 130 may be fixedly coupled to the housing 902. The motor 906 may include a diaphragm 908 disposed in a chamber 910. A periphery 940 of the diaphragm 908 may be retained in a groove 942 formed in the probe 900. The chamber 910 may include a first passage 912 for communicating a pneumatic pressure to a first surface 914 of the diaphragm 908 and a second passage 916 for communicating a pneumatic pressure to a second surface 918 of the diaphragm 908. Alternating pneumatic pressure between the first passage 912 and the second passage 916 displaces the diaphragm 908 in opposing directions, causing the diaphragm 908 to oscillate.

While the probes described herein are described as having a motor that may include a diaphragm, the disclosure is not intended to be so limiting. Rather, any device operable to oscillate an inner cutting member/interior assembly may be used. As such, the probes described herein are provided merely as examples.

The inner cutting member 140 is coupled to the diaphragm 908. Consequently, the inner cutting member 140 is made to oscillate within the probe 900 relative to the outer cutting member 130. In some instances, the inner cutting member 140 may be coupled to the diaphragm 906 by a tube 920 and a hollow coupling 922. The inner cutting member 140, the hollow coupling 922, and the tube 920 form an interior assembly 924 and define a passage 925 that may be utilized for aspirating fluid, tissue, and other material from the eye. In some instances, the interior assembly 924 may exclude the hollow coupling. Thus, in some instances, the tube 920 and the inner cutting member 140 may be directly coupled, such as by welding, an interference fit, threaded connection, or in any other suitable manner. Alternatively, the tube 920 may be eliminated and the inner cutting member 140 may be formed at a desired length as a result. Thus, in some instances, the interior assembly 924 may or may not include the coupling 922 and/or the tube 920.

Seals 944, 946, 948, and 950 may be included to prevent and/or substantially reduce the passage of fluid from the chamber 910. One or more of the seals 944, 946, 948, 950 may be similar to each other. In other instances, one or more of the seals may be different. Other implementations may include additional, fewer, or different seals than those described. In some implementations, the seals 944-950 may also provide low resistance to movement of the interior assembly 924. In some instances, the seals 944-950 may be o-rings. However, the seals 944-950 may be any suitable seals. In other instances, static flex seals may be used. That is, a seal having an outer periphery and an inner periphery thereof secured to the housing of the probe. A static flex seal provides relative movement of components while maintaining a seal therebetween.

The probe 900 may also include a stroke limiter 960. The stroke limiter 960 includes a threaded surface 962. The stroke limiter 960 is threadably retained in an interior sleeve 964. The interior sleeve 964 includes an inner threaded surface 966 that cooperatively engages the threaded surface 962 of the stroke limiter 960. The stroke limiter 960 may also include a geared surface 970. In some instances, the geared surface 970 may include a plurality of gear teeth 972 extending in a direction parallel to a longitudinal axis 974 of the stroke limiter 960.

The probe 900 may also include a piezoelectric linear motor (interchangeably referred to as "piezoelectric motor") 926. In some implementations, the piezoelectric motor 926 may be an ultrasonic linear actuator. The piezoelectric motor 926 may be fixedly secured within the housing 902. For example, the piezoelectric motor 926 may be retained within a receptacle 927 formed in the housing 902. In some instances, the piezoelectric motor 926 may be secured within the housing 902 with a fastener, adhesive, interference fit, retaining clip, or in any other desired manner. Power may be provided to the piezoelectric motor 926 via a cable 928 extending through the housing 902. In some implementations, the cable 928 may be coupled to a surgical console. In some instances, the piezoelectric motor 926 may be an SQL-1.8-6 SQUIGGLE® Piezo Linear Motor produced by New Scale Technologies, Inc., of 121 Victor Heights Parkway, Victor, N.Y. 14564. However, other types of piezoelectric motors may be used and are within the scope of the disclosure.

The piezoelectric motor 926 may include a lead screw 930 and a gear 976 coupled thereto. The gear 976 may include a geared surface 978 having a plurality of gear teeth 980 also extending in a direction parallel to the longitudinal axis 974. The plurality of gear teeth 972 intermesh with the plurality of gear teeth 980.

Application of an AC drive voltage signal at a first phase offset causes lead screw 930 to rotate in a first direction. Application of an AC drive voltage signal at second phase offset different than the first phase offset causes lead screw 930 to rotate in a second direction opposite the first direction. In operation, the piezoelectric motor 926 rotates the lead screw 930 in the first or second direction, which, in turn, rotates the gear 976. The gear 976, in turn, rotates the stroke limiter 960 as a result of the intermeshing gear teeth 972, 978. In response to the rotation of the lead screw 930 in either the first or second direction, the stroke limiter 960 is one of extended (i.e., move the stroke limiter 960 in the direction of arrow 932) or retracted (i.e., move the stroke limiter 960 in the direction of arrow 934) the relative to the interior sleeve 964 as a result of the cooperatively engaging threaded surfaces 962 and 966. The stroke limiter 960 and the gear 976 are configured to slide longitudinally relative to each other because of the longitudinal orientation of the intermeshing gear teeth 972, 980

A surface 937 of the stroke limiter 960 may engage a surface 936 of the coupling 922 to define a fully retracted position of the inner cutting member 140. In response to the AC drive voltage signal applied to the piezoelectric motor 926, the position of the stroke limiter 960 is changed, and a location at which the moveable member 931 engages, for example, the coupling 922 changes. Consequently, by adjusting a position of the stroke limiter 960 via the AC drive voltage applied to the piezoelectric motor 926, the amount of movement of the inner cutting member 140 in the direction of arrow 934 may be altered, thereby changing the size of the port 120. It is noted that movement of the inner cutting member 140 in the direction of arrow 934 corresponds to an opening of the port 120 shown, for example, in FIGS. 4-8.

In some instances, a user may adjust a position of the stroke limiter 960 and, hence, the port size, for example, by interacting with a control provided on the probe 900, a control provided on the surgical console to which the probe 900 is coupled, or on an input device, such as an input device coupled to the surgical console. Example input devices may include a touch screen, button, slider, footswitch, or other input device, coupled to the surgical console. Other input devices may also be used. Control inputs may be transmitted to the piezoelectric motor 926 via the cable 928.

While the stroke limiter is described as engaging the coupling 922, the stroke limiter 960 may be adapted to engage other parts of the probe 900. In other instances, another portion of the interior assembly 924 may engage the stroke limiter 960. For example, tube 920 or inner cutting member 140 may engage the surface 937 of the stroke limiter 960. In still other instances, for example, as shown in FIG. 10, a collar 1000 may be coupled to the tube 920, and the surface 937 of the stroke limiter 960 contact a surface 1002 of the collar 1000 to define the size of the port 120. A collar, similar to collar 1000, may also be used in one or more of the other example probes described herein. Further, in some instances, the coupling 922 may be eliminated altogether, and the inner cutting member 140 may be coupled to the tube 920 in another way. For example, the inner cutting member 140 may be directly coupled to the tube 920, such as by welding, an interference fit, threaded connection, or in any other suitable manner. Further, the configuration shown in FIG. 10 is not limited to the example probe 900 shown in FIG. 9, but may be incorporated into any of the example probes described herein. That is, one or more of the other example probes described herein may include a collar that may be similar to collar 1000 to engage a stroke limiter.

While the probe 900 is described above as including a piezoelectric motor 926, any suitable rotational drive motor may be used. For example, in some implementations, a vitrectomy probe may include a stepper motor. In other implementations, a DC motor acting against a torsional spring may be used to adjust the port size. These are provided merely as examples. Thus other rotational drive devices may be utilized to adjust the port size.

The other example probes disclosed herein are described primarily with respect to the features related to the adjustment of the port size. As such, other aspects of the example probes may be similar to one or more aspects described above with respect to probe 900. For example, the outer cutting member of one or more of the probes described herein may be fixedly attached to the probe housing. Also, one or more of the example probes may include similar seals at one or more locations within the example probes similar to probe 900. One or more other features may also be similar.

Figure 11:
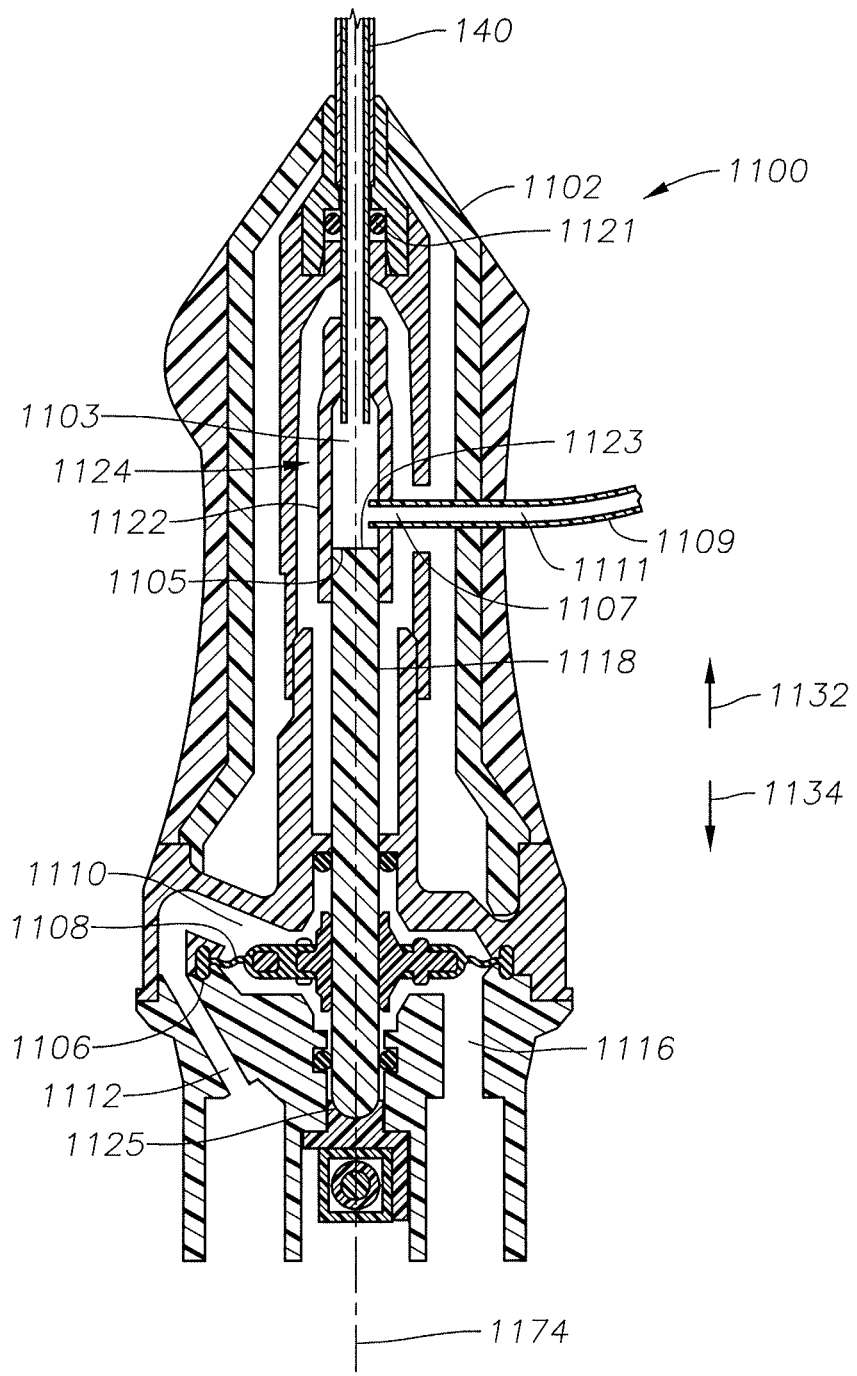
FIG. 11 shows a cross-sectional view of an example vitrectomy probe that includes a stroke limiter having an inclined surface.

FIGS. 11-13 illustrate another example probe 1100. FIG. 11 is a cross sectional view of the probe 1100, and FIG. 12 is a partial cross-sectional view of the probe 1100 along a plane different than the one shown in FIG. 11. For example, the cross-sectional view shown in FIG. 12 may be at a 90 degree offset about the longitudinal axis 1174. FIG. 12 shows internal components for controlling a size of the port 120 of the probe 1100. The probe 1100 may be similar to the probe 900, discussed above. Accordingly, the probe 1100 may include a motor 1106 disposed in a chamber 1110. The motor 1106 may include a diaphragm 1108 disposed in a fluidic chamber 1110. The diaphragm 1108 may be retained within the housing 1102. Similar to probe 900, a first passage 1112 and a second passage 1116 may be formed in the probe 1100 and are operable to communicate pneumatic pressure to opposing sides of the diaphragm 1108 to oscillate the diaphragm 1108, as shown in FIG. 11. While FIGS. 11 and 12 show the probe 1100 as including a motor having a diaphragm, other types of motors may be used. That is, probe 1100 may include any suitable motor operable to oscillate the inner cutting member 140.

Referring again to FIG. 12, the probe 1100 may also include an interior assembly 1124. The interior assembly 1124 may be similar to the interior assembly 924, described above. In this example, the interior assembly 1124 includes inner cutting member 140, a coupling 1122, and an extension 1118. An end of the inner cutting member 140 may be received into an interior of the coupling 1122. Further, the interior assembly 1124 defines a passage 1103. In some instances, the interiors of the inner cutting member 140 and the coupling 1122 defines the passage 1103. The passage 1103 includes a terminal end 1105.

Although FIG. 12 shows a coupling 1122 extending between the extension 1118 and the inner cutting member 140, in other instances, the coupling 1122 may be eliminated. In other instances, the coupling 1122 may form an integral part of the extension 1118. In still other instances, the inner cutting member 140 may extend and be coupled to the extension 1118. Thus, the described implementation is provided merely as an example.

An opening 1107 may be formed in the tube 1120 and a conduit 1109 may be coupled to the coupling 1122. A passage 1111 defined by the conduit 1109 communicates with passage 1103. Thus, materials aspirated through the interior assembly 1124 may be carried way from the probe 1100 via the conduit 1109. The conduit 1109 may be formed from tubing or any other suitable conduit. In implementations where the coupling 1122 is eliminated, the inner cutting member may be configured similarly to the coupling 1122. That is, the inner cutting member 140 may have a terminal end and an opening formed in the inner cutting member 140 proximate the terminal end providing communication between a passage formed by the inner cutting member and passage 1111 of the conduit 1109.

In still other implementations, the interior assembly 1124 may include the inner cutting member 140, a tube 1120, and extension 1118, as shown in FIG. 41. An end of the inner cutting member 140 may be received into the passage 1103 of the tube 1120, and the tube 1120 may be joined with the extension 1118. In some instances, the tube 1120 may form an integral part of the extension 1118.

The probe 1100 may also include a stroke limiter 1160 and a piezoelectric motor 1126. The extension 1118 extends through and is coupled to the motor 1106. For the implementation shown, the extension 1118 is coupled to diaphragm 1108. The probe 1100 may also include seals 1121 disposed within the pneumatic chamber 1110. The seals 1121 may provide a seal around the extension 1118 to prevent and/or substantially reduce passage of fluid thereby. The seals 1121 may be o-ring seals or any other suitable type of seal. Other implementations may include additional, fewer, or different seals than those described.

The extension 1118 may include a first end surface 1123 and a second end surface 1125. The extension 1118 may be coupled to the tube 1120. In some instances, for example, the first end surface 1123 may be in contact with the terminal end 1105 of the inner cutting member 140. In some instances, the first end surface 1123 may be coupled to the terminal end 1105 by welding, an adhesive, a press fit, or in any other suitable manner. Thus, as the motor 1106 is oscillated, the inner cutting member 140, tube 1120 and the extension 1118 are correspondingly oscillated in the directions of arrows 1132 and 1134.

In some implementations, the extension 1118 may have a tubular shape. However, in other implementations, the extension 1118 may have other shapes. For example, the outer surface of the extension 1118 may be defined by a plurality of facets. Further, in some implementations, the second end surface 1125 may be semi-hemispherical. However, the second end surface 1125 may be flat or have any other suitable shape.

The piezoelectric motor 1126 may be similar to the piezoelectric motor 926 described above. In other instances, the piezoelectric motor 1126 may be replaced by other rotational drive motors, such as those also described above. Power may be provided to the piezoelectric motor 1126 via a cable 1128. The cable 1128 may extend through the housing 902.

The piezoelectric motor 1126 may include a lead screw 1130. Opposing ends of the lead screw 1130 may be rotatably retained within recesses 1170 formed in the housing 1102. As such, the lead screw 1130 is rotatable within the recesses 1170 but otherwise fixed relative to the housing 1102. The piezoelectric motor 1126 may be coupled to the stroke limiter 1160. While the piezoelectric motor 1126 of the example probe 1100 is shown as disposed substantially perpendicular to a plane passing through the centerlines of the first and second passages 1112, 1116, this configuration is provided merely as an example. As such, the piezoelectric motor 1126 may be oriented in other ways relative to the first and second passages 1112, 1116 or other portions of the probe 1100. As such, the example probe 1100 shown in FIGS. 11-13 are provided merely as an example.

Referring to FIG. 13, the stroke limiter 1160 may include a contact surface 1162 having an inclined portion 1164 flanked by level surfaces 1166, 1168. In some instances, the contact surface 1162 may define a groove 1169. The end 1125 of the extension 1118 may be received within the groove 1169 and be slideable therein.

Application of an AC drive voltage signal of a first phase offset to the piezoelectric motor 1126 may cause rotation of the lead screw 1130 in a first direction such that the stroke limiter 1160 moves in the direction of arrow 1136. Application of an AC drive voltage signal of a second phase offset may cause rotation of the lead screw 1130 in a second direction, opposite the first direction, such that the stroke limiter 1160 moves in the direction of arrow 1138. In operation, as the stroke limiter 1160 is moved in the direction of arrow 1136, movement of the inner cutting member 140 in the direction of arrow 1134 increases (and the size of port 120 increases) due to the slope of the inclined portion 1164 of the contact surface 1162. Movement of the inner cutting member 140 in the direction of arrow 1134 continues to increase (as does the size of port 120) as the stroke limiter 1160 is moved in the direction of arrow 1136 until level surface 1168 resides adjacent the end 1125 of the extension 1118. Alternately, as the stroke limiter 1160 is moved in the direction of arrow 1138, movement of the inner cutting member 140 in the direction of arrow 1134 decreases (and the size of port 120 decreases) due to the slope of the inclined portion 1164 of the contact surface 1162. Movement of the inner cutting member 140 in the direction of arrow 1134 continues to decrease (as does the size of port 120) as the stroke limiter 1160 is moved in the direction of arrow 1138 until level surface 1166 resides adjacent the end 1125 of the extension 1118.

While the contact surface 1162 has the orientation as shown in FIG. 11, in other implementations, the orientation of the contact surface 1162 may be reversed, and the effect on the size of port 120 may be opposite as that described above with movement of the stroke limiter 1160 in the directions of arrows 1136, 1138.

A user may adjust a position of the stroke limiter 1160 in a manner similar to that described above. That is, in some instances, a user may interact with one or more controls provided on one or more of the probe itself, the surgical console to which the probe 1100 is coupled, or an input device. An input device of a type described above may be used. A control signal, e.g., an AC drive voltage signal of a type described above, may be transmitted to the piezoelectric motor 1126 via the cable 1128. A position of the stroke limiter 1160 may be adjusted one or more times before, during, or after a surgical procedure.

Figure 14A:
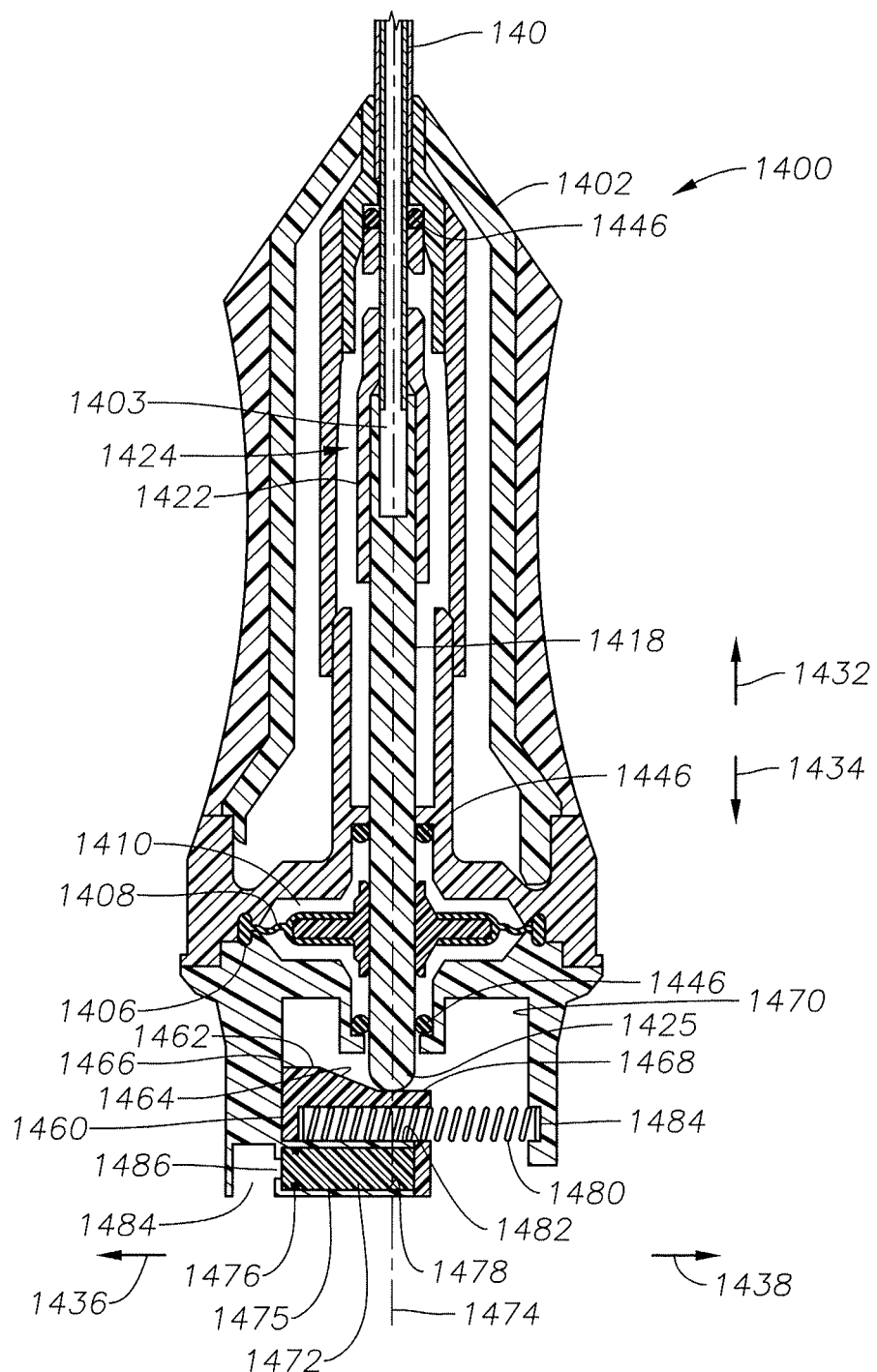
FIGS. 14A and 14B are cross-sectional views of another example vitrectomy probe that includes a stroke limiter with an inclined surface.
Figure 14B:
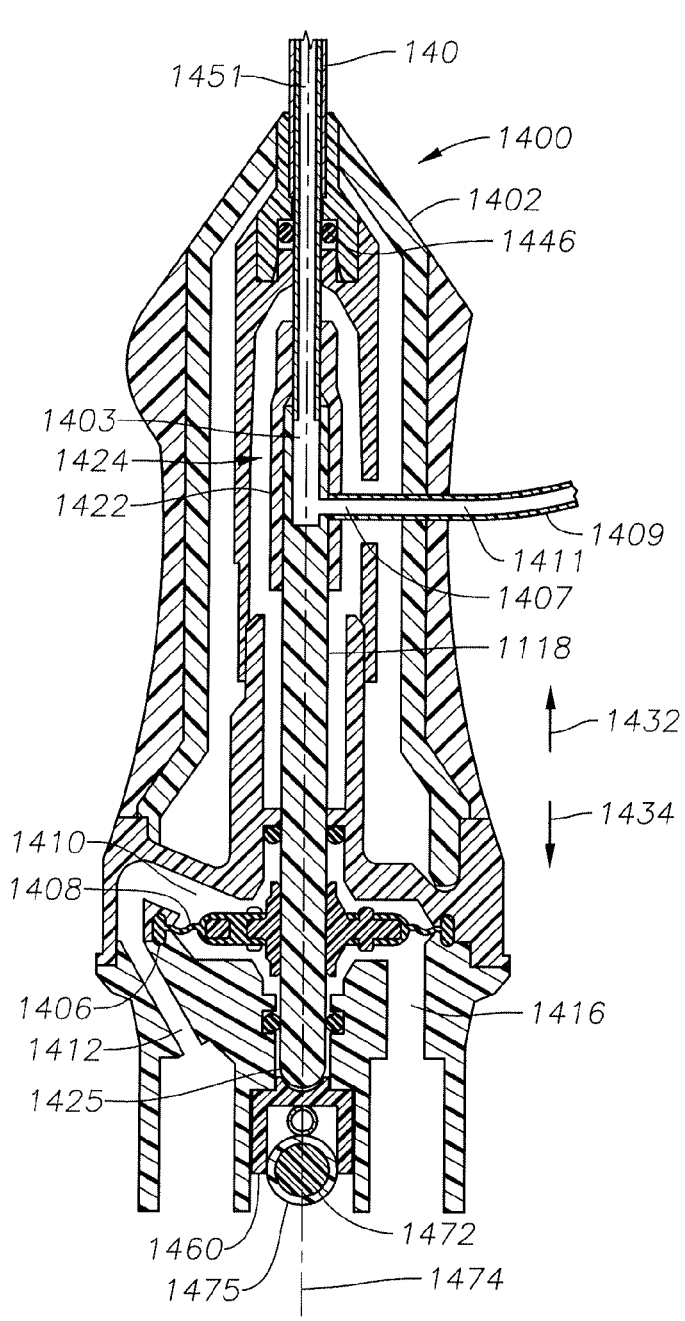
Figure 15:
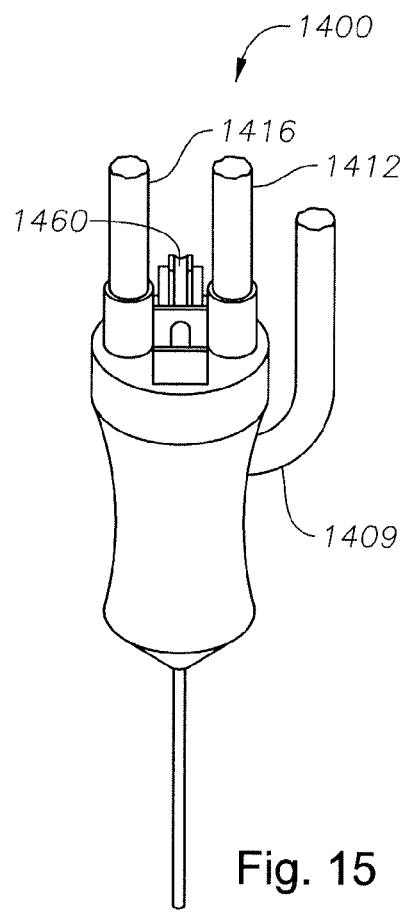
FIG. 15 is a perspective view of the example vitrectomy probe of FIG. 14 showing a conduit for passage of aspirated material.

FIGS. 14A, 14B, and 15 show another example probe 1400. FIG. 14A is a detail cross-sectional view of the example probe 1400 taken along a plane passing through probe 1400 different than that of the plane defining the cross-sectional view shown in FIG. 14B. For example, the cross-section shown in FIG. 14A may be approximately 90° offset from the cross-sectional view shown in FIG. 14B taken about axis 1474.

As shown in FIGS. 14A and 14B, probe 1400 may be similar to probe 1100, described above. Similar to probe 1100, the probe 1400 may include a motor 1406 disposed in a chamber 1410. In some instances, the motor 1406 may include a diaphragm 1408. In other instances, the motor 1406 may not include a diaphragm. Thus, the motor 1406 may be any type of device operable to oscillate the inner cutting member 140.

As shown in FIGS. 14A and 14B, the diaphragm 1408 may be disposed in a pneumatic chamber 1410. Seals 1446 may be included to prevent and/or substantially reduce fluid from passing into or out of chamber 1410. Although two seals are shown, in some implementations, additional, fewer, or no seals may be included in the probe 1400. As explained above, pneumatic pressure may be applied to opposing sides of the diaphragm 1408 via passages 1412 and 1416 to oscillate the diaphragm 1408. An extension 1418 may also be included. The extension 1418 may be similar to the extension 1118, described above, and may form a part of an interior assembly 1424. Thus, in some instances, the interior assembly 1424 may include the inner cutting member 140, a coupling 1422, and the extension 1418. In some implementations, an end of the inner cutting member 140 may be received into the coupling 1422 and secured thereto. In some instances, an end of the extension 1118 may also be received into the coupling 1422. In some instances, coupling 1422 may be integral with the extension 1418. In still other implementations, the coupling 1422 may be eliminated. Thus, in some instances, the inner cutting member 140 may be coupled directly to the extension 1418.

In the illustrated example, the extension 1418 may include a cavity 1403 and an opening 1407. Aspirated materials may pass through a lumen 1451 formed by the inner cutting member 140, the cavity 1403 formed by the extension 1418, through opening 1407, and out of the probe 1400 through passage 1411 of conduit 1409. The conduit 1409 may be similar to conduit 1109 described above. Further, similar to the extension 1118, the extension 1418 may extend through the diaphragm and may be coupled thereto such that the extension 1418 oscillates in the directions of arrow 1432 and 1434 as the diaphragm 1408 oscillates in response to the applied pneumatic pressure. Pneumatic pressure may be conducted into the probe 1400 to the diaphragm 1408 via conduits 1412, 1416.

A stroke limiter 1460 may also be included. The stroke limiter 1460 may be disposed in a chamber 1470 formed in housing 1402 of the probe 1400. In some implementations, the stroke limiter 1460 may be disposed between the conduits 1412, 1416 defining the passages that communicate fluid pressure to the opposing sides of the diaphragm 1408. However, in other implementations, the stroke limiter 1460 may be positioned in other locations within the probe 1400.

The stroke limiter 1460 may include a piston 1472 that is slideable received within a chamber 1475. A seal 1476 may be disposed between the piston 1472 and an interior surface 1478 of the chamber 1475. The seal 1476 may be similar to one or more of the seals described herein and may prevent and/or substantially reduce passage of fluid between the piston 1472 and the interior surface 1478. A biasing member 1480 is received within a recess 1482 formed in the stroke limiter 1460. The biasing member 1480 is disposed between the stroke limiter 1460 and an interior surface 1484 of the chamber 1470. In some instances, the biasing member 1480 may be a spring, such as a coil spring. However, the biasing member 1480 may be any resilient member operable to apply a biasing force to the stroke limiter 1460.

The probe 1400 may also include a passage 1484 that communicates with the chamber 1475 via opening 1486. In some instances, pneumatic pressure may be transmitted through the passage 1484, through the opening 1486, and into the chamber 1475 to displace the piston 1472. In other instances, hydraulic pressure may be applied. As the pressure transmitted to the chamber 1475 increases, the stroke limiter 1460 is displaced in the direction of arrow 1438. Also, as the pressure within the chamber 1475 increases, the biasing member 1480 may be compressed. As the pressure within the chamber 1475 is decreased, the biasing force of the biasing element 1480 urges the stroke limiter 1460 in the direction of arrow 1436. Displacement of the stroke limiter 1460 within the chamber 1470 ceases when the applied pressure is balanced by the biasing force of the biasing member 1480.

Figure 16:
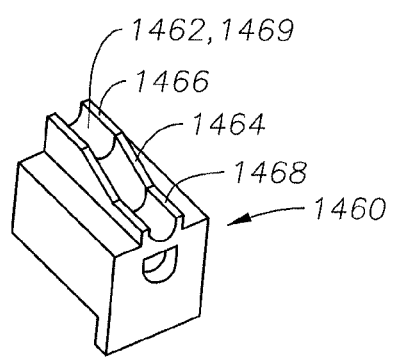
FIG. 16 is a perspective view of an example stroke limiter of the example vitrectomy probe of FIGS. 14A, 14B, and 15.

Similar to the stroke limiter 1160, the stroke limiter 1460 may also include a contact surface 1462 that may include an inclined portion 1464 disposed between level portions 1466 and 1468. In some instances, as shown in FIG. 16, the contact surface 1462 may define a groove 1469 extending therealong. In other instance, though, the contact surface 1462 may be flat or substantially flat. An end 1425 of the extension 1118 may be received within the groove 1469 and be slideable therein.

In operation, as the stroke limiter 1460 is moved in the direction of arrow 1438, movement of the inner cutting member 140 in the direction of arrow 1434 decreases (and the size of port 120 decreases) due to the slope of the inclined portion 1464 of the contact surface 1462. Movement of the inner cutting member 140 in the direction of arrow 1434 continues to decrease (as does the size of port 120) as the stroke limiter 1460 is moved in the direction of arrow 1438 until level surface 1466 resides adjacent an end 1425 of the extension 1418. Alternately, as the stroke limiter 1460 is moved in the direction of arrow 1136, movement of the inner cutting member 140 in the direction of arrow 1434 increases (and the size of port 120 decreases) due to the slope of the inclined portion 1464 of the contact surface 1462. Movement of the inner cutting member 140 in the direction of arrow 1434 continues to increase (as does the size of port 120) as the stroke limiter 1460 is moved in the direction of arrow 1136 until level surface 1468 resides adjacent the end 1425 of the extension 1418.

While the contact surface 1462 has the orientation as shown in FIG. 14, in other implementations, the orientation of the contact surface 1462 may be reversed, and the effect on the size of port 120 may be opposite as that described above with movement of the stroke limiter 1460 in the directions of arrows 1436, 1438.

The remainder of probe 1400 may be similar to and may operate similarly to any one of the probes explained herein. For example, for implementations utilizing a diaphragm as part of a motor, the diaphragm 1408 may be oscillated, such as by alternating application of fluidic pressure (e.g., pneumatic or hydraulic) to opposing surfaces of the diaphragm 1408. The oscillating diaphragm 1408 may operate interior assembly 1424 to sever tissue. The severed tissue may be aspirated via the lumen 1451 of the inner cutting member 140, cavity 1403, and passage 1411 of the conduit 1409.

Further, pneumatic pressure applied to the piston 1472 may be adjusted by a user in a manner similar to that described above. For example, the user may interact with a control provided on one or more of the probe 1400, the surgical console, or an input device.

FIGS. 17-21 show another example probe 1700. The probe 1700 may include a motor 1706 disposed in a fluidic chamber 1710. In some implementations, the motor 1706 may include a diaphragm 1708, similar to those described above. However, in other implementations, the motor 1708 may be any other suitable device operable to generate an oscillation. Fluidic pressure may be conducted to the diaphragm 1708 via conduits 1712, 1716. Material may be aspirated from the probe 1700 via the conduit 1709. Additionally, the motor 1706 may operate in a similar manner to those described above to oscillate an interior assembly 1724. The interior assembly 1724 may include an extension 1718, a coupling 1722, and inner cutting member 140. The interior assembly 1724 may have other configuration. That is, the interior assembly 1724 may be similar to one or more of the other interior assemblies described herein. The extension 1718 may extend through at least a portion of housing 1702. The extension 1718 may be coupled to the diaphragm 1708 at one end. As such, the interior assembly 1718 may be made to oscillate with the diaphragm 1708. The probe 1700 may also include seals 1740 to prevent and/or substantially reduce the passage of fluid between the housing 1702 and the extension 1718 and stroke limiter 1726.

To control a size of port 120 (as shown in FIGS. 4-8, for example), the probe 1700 may include the stroke limiter 1726. The stroke limiter 1726 may extend through an opening 1744. An interior wall 1746 defining opening 1744 may have a threaded surface 1701 that engages a corresponding threaded surface 1703 formed on an exterior of the stroke limiter 1726. As such, the stroke limiter 1726 may be made to move in the direction of arrow 1732 (i.e., extended) when rotated in a first direction and in the direction of arrow 1734 (i.e., retracted) when rotated in a second direction, opposite the first direction. A size of the port 120 is defined by a location where the interior assembly 1724 contacts the stroke limiter 1726. Thus, retraction of the stroke limiter 1726 in the direction of arrow 1734 increases a distance between the stroke limiter 1726 and the interior assembly 1724, thereby increasing a size of the port 120. Extension of the stroke limiter 1726 in the direction of arrow 1732 decreases a distance between the stroke limiter 1726 and the interior assembly 1724, thereby decreasing a size of the port 120. While in some instances, the stroke limiter 1726 may contact a portion of the interior assembly 1724, the scope is not so limited. For example, in other instances, the stroke limiter 1726 may contact a portion of the motor 1706. For example, in some instances utilizing a diaphragm as a motor, the stroke limiter 1726 may contact the diaphragm 1708. The stroke limiter 1726 may also include a gear 1748 having a plurality of teeth 1750 formed along a perimeter thereof.

Figures 17, 18:
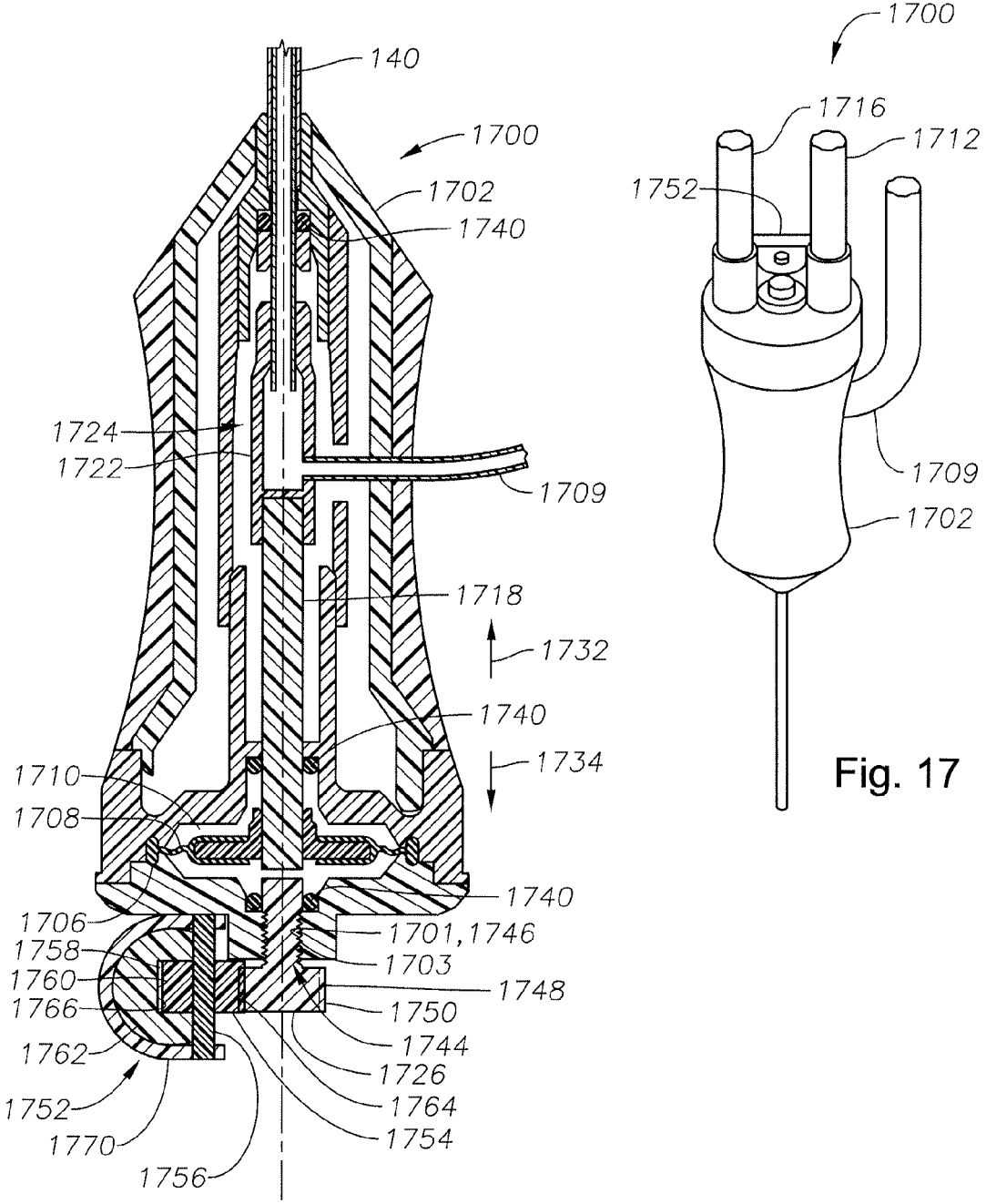
FIGS. 17-20 show an example vitrectomy probe that includes a rack and pinion device for adjusting a port size.
Figure 19:
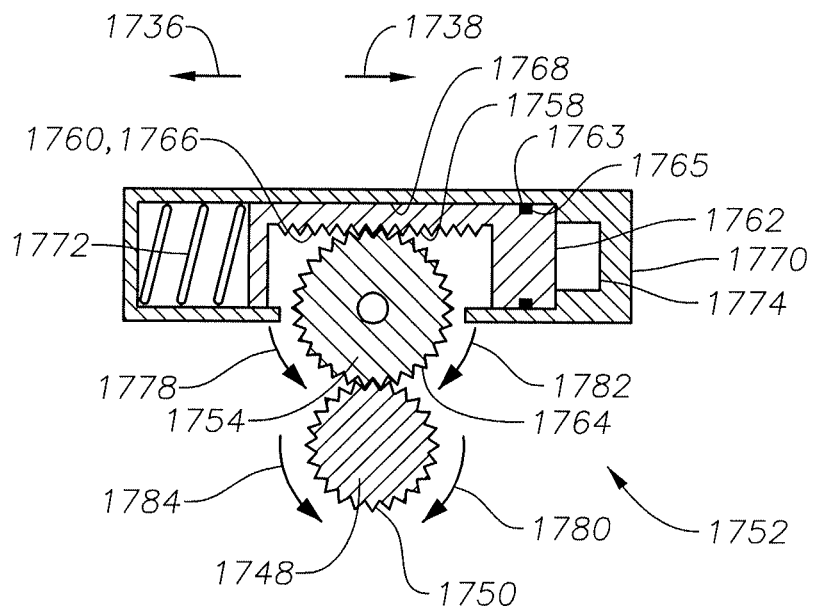

The stroke limiter 1726 may be extended or retracted via a rack and pinion arrangement 1752. The arrangement 1752 may include a pinion gear 1754 pivotal on a shaft 1756 and a rack gear 1758 formed on a surface 1760 of a piston 1762. Referring to FIGS. 18 and 19, the pinion gear 1754 may include a plurality of teeth 1764 formed on a perimeter thereof. A plurality of teeth 1766 formed on the surface 1760 engages the plurality of teeth 1764 of the pinion gear 1754.

Referring to FIG. 19, the piston 1762 resides in a chamber 1768 formed in a housing 1770. A biasing member 1772 may be disposed in the chamber 1768 between the housing 1770 and the piston 1762. In some instances, the biasing member 1762 may be a spring, such as a coil spring. A seal 1763 may be disposed in a groove 1765 of the piston 1762 to form a seal between the piston 1762 and an interior surface of the chamber 1768. The seal 1763 may be similar to one or more of the other seals described herein and may prevent and/or substantially reduce passage of fluid from a portion 1774 where fluidic pressure is introduced into the chamber 1768.

Fluidic pressure (e.g., pneumatic or hydraulic) may be introduced into the portion 1774 of the chamber 1768. The fluidic pressure may be introduced through a conduit 1776 (shown in FIG. 20). As fluidic pressure increases within the chamber 1768 above a biasing force applied by the biasing member 1772, the piston 1762 is displaced in the direction of arrow 1736. Displacement of the piston 1762 in the direction of arrow 1736 cause the pinion gear 1754 to rotate about shaft 1756 in the direction of arrow 1778 as a result of the intermeshing gear teeth. The rotating pinion gear 1754 causes rotation of the gear 1748 (and, hence, the stroke limiter 1726) in the direction of arrow 1780. In an example implementation, rotation of the stroke limiter 1726 in the direction of arrow 1780 may cause the stroke limiter 1726 to extend in the direction of arrow 1732 due to the intermeshing threaded surfaces 1701, 1703. As a result, a distance between the stroke limiter 1726 and the interior assembly 1724 is decreased. Consequently, the size of port 120 is reduced.

A reduction of fluidic pressure within the portion 1774 of chamber 1768 may cause the biasing member 1772 to displace the piston 1762 in the direction of arrow 1738, causing the pinion gear 1754 to rotate in the direction of arrow 1782. This, in turn, causes the gear 1748 and, hence, the stroke limiter 1726 to rotate in the direction of 1784. In some implementations, rotation of the stroke limiter 1726 in the direction of arrow 1784 may cause the stroke limiter 1726 to retract in the direction of arrow 1734 due to the intermeshing threaded surfaces 1701, 1703. Movement of the stroke limiter 1726 in the direction of arrow 1734 increases a distance between the stroke limiter 1726 and the interior assembly 1724. Consequently, the size of the port 120 is increased.

While FIGS. 17-21 show an example probe 1700, it is understood that the rotation of the stroke limiter 1726 in a particular direction to cause a longitudinal movement within the probe may be reversed, for example, by reversing the direction of the engaging threads 1701 and 1703 of the interior wall 1746 and the stroke limiter 1726, respectively. Further, the rate at which the stroke limiter 1726 is extended or retracted may be altered by the pitch of the engaging threads 1701, 1703. Still further, the rate at which the stroke limiter 1726 is extended or retracted may be selected by, for example, adjusting the gearing ratio between the pinion gear 1754 and the gear 1748.

The probe 1700 may be similar in other respects to one or more of the example probes described herein. Further, user input for adjusting a position of the stroke limiter 1726 may be inputted in a manner similar to that described above.

Figure 22:
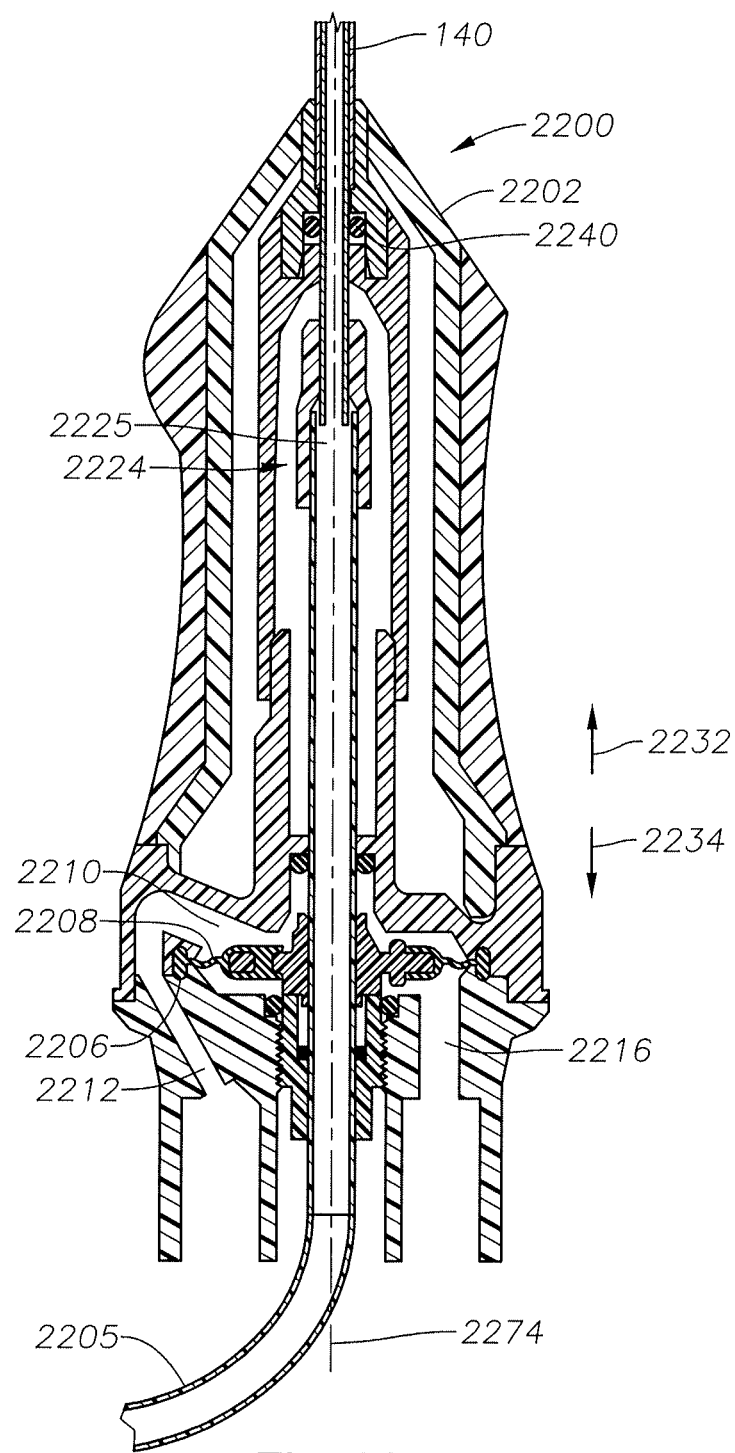
Figure 23:
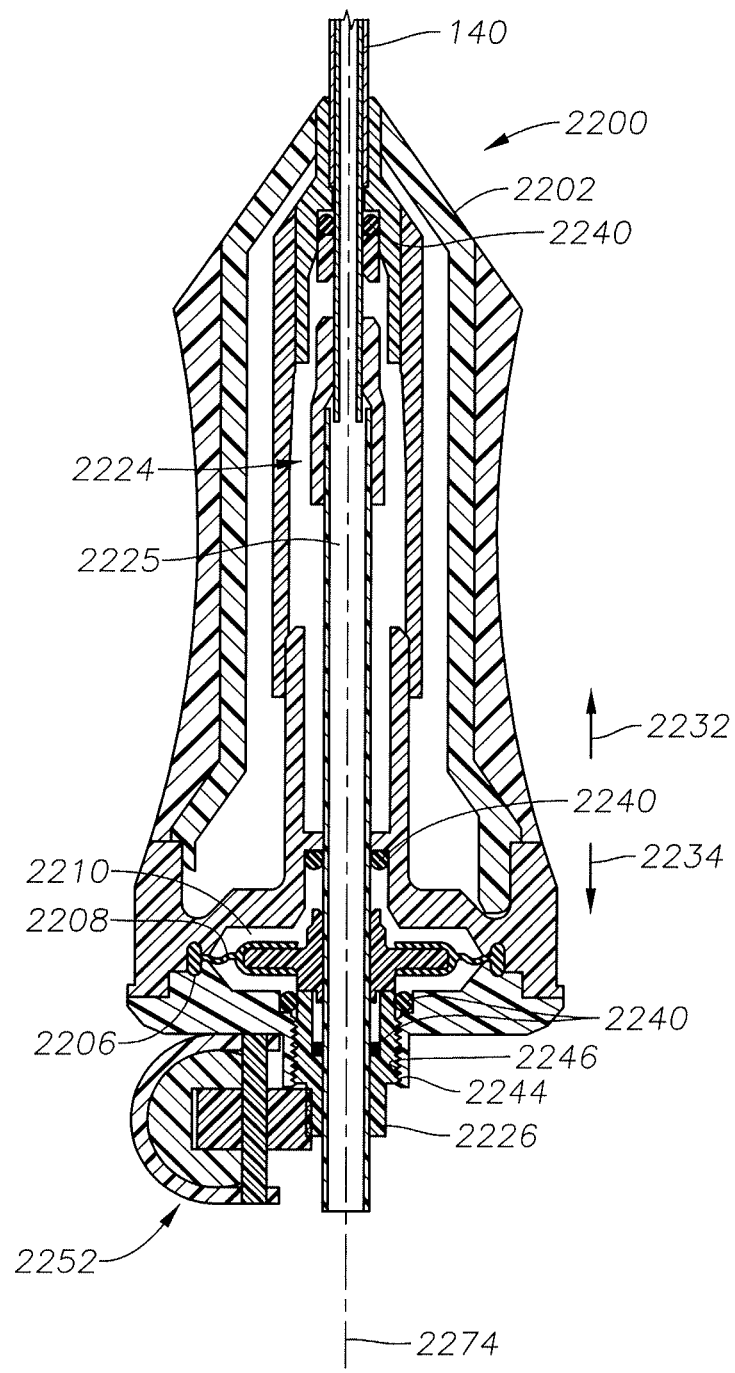
Figure 24:
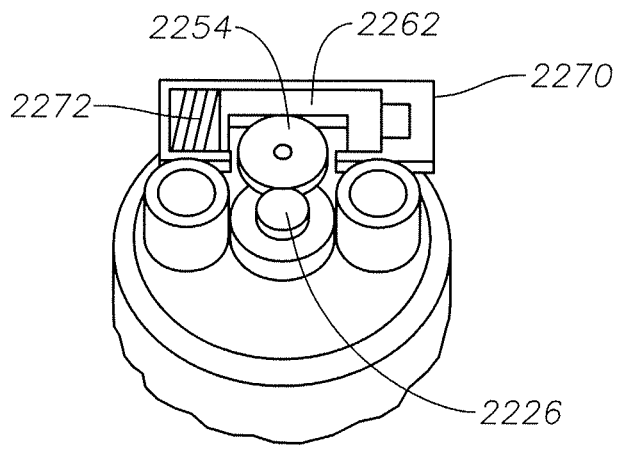
FIG. 24 is a transverse cross-sectional view of the example probe of FIGS. 21-23 showing an example arrangement operable to adjust a position of a stroke limiter.

FIGS. 22-24 illustrate another example vitrectomy probe 2200. FIG. 22 is a cross-sectional view of the example probe 2200 taken along a plane passing through probe 2200 different than that of the plane defining the cross-sectional view shown in FIG. 23. For example, the cross-section shown in FIG. 22 may be approximately 90° offset from the cross-sectional view shown in FIG. 23 taken about axis 2274. In some respects, the probe 2100 may be similar to the probe 1700. For example, the probe 2200 may include a motor 2206 disposed in a chamber 2210. In some instances, the motor 2206 may include a diaphragm 2208 coupled at an edge thereof to housing 2202. Pneumatic pressure may be applied to opposing sides of the diaphragm 2208 via passages 2212 and 2216 to oscillate the diaphragm 2208. However, in other instances, the motor 2206 may not include a diaphragm.

An interior assembly 2224 (which may be similar to one or more of the interior assemblies described herein) extends through and is coupled to the motor 2206. In the example shown, the interior assembly 2224 is coupled to the diaphragm 2208. Thus, operation of the motor 2206 causes the interior assembly 2224 to oscillate within the probe 2200. The interior assembly 2224 defines a passage 2225 through which material may be aspirated from the probe 2200. The probe 2200 may also include a stroke limiter 2226 and an arrangement 2252, similar to the arrangement 1752 described above. The stroke limiter 2226 extends through an opening 2244, and, similar to the example probe 1700 above, the stroke limiter 2226 may threadingly engage an interior wall 2246 defining the opening 2244. Thus, as the stroke limiter 2226 is rotate about axis 2274, the stroke limiter 2226 one of extends in the direction of arrow 2232 or retracts in the direction of arrow 2234. Further, the interior assembly 2224 extends through a passage 2229 formed in the stroke limiter 2226. Consequently, aspirated materials may be passed through the passage 2225 and to an aspiration conduit 2205 without the need for an alternative path, such as the path defined through the conduit 1709 of the probe 1700 shown in FIG. 17.

The stroke limiter 2226 may also include an ends surface 2227 that is operable to contact the diaphragm 2208. Thus, as the stroke limiter 2226 is made to extend or retract within the probe 2200, a location where the diaphragm 2208 and the stroke limiter 2226 contact each other is changed, thereby adjusting a size of the port 120. The probe 2200 may also include seals 2240 that may be similar to those described above.

Figure 25:
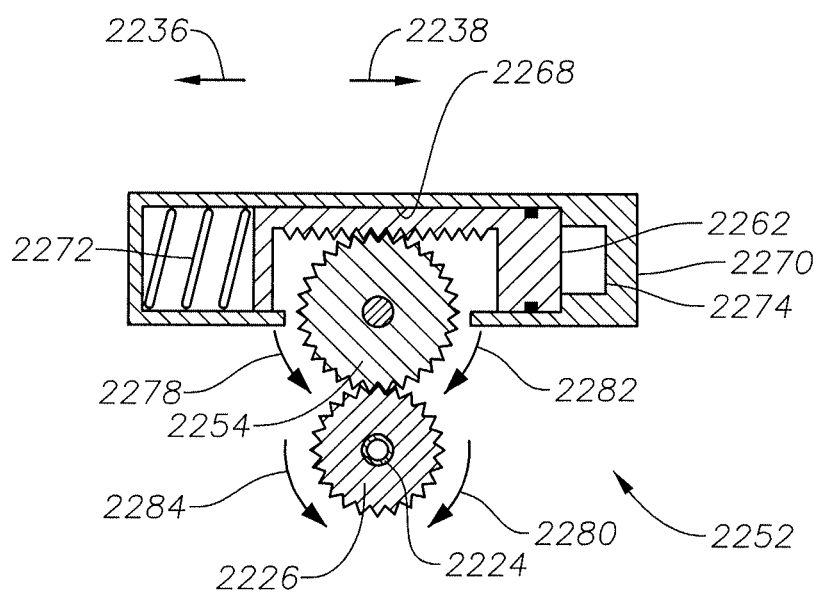
FIG. 25 shows a cross-sectional view of an example arrangement of the example probe of FIGS. 21-24.

The arrangement 2252 may be used to adjust the position of the stroke limiter 2226 within the probe 2200. The arrangement 2252 may be similar to and operate in a manner similar to the arrangement 1752. Thus, referring to FIG. 25, fluidic pressure (e.g., pneumatic or hydraulic pressure) may be introduced into a portion 2274 of a chamber 2268 formed in housing 2270. As the fluidic pressure is increased, piston 2262 is made to move in the direction of arrow 2236 against a biasing force from biasing member 2272 to cause pinion gear 2254 to rotate in a first direction 2278, for example, as a result of intermeshing gears. Rotation of the pinion gear 2254 in the first direction 2278 causes the stroke limiter to rotate in a direction 2280 due to intermeshing gears. As fluidic pressure is reduced and the biasing force from biasing member 2272 moves the piston 2262 to move in the direction of arrow 2238, the pinion gear 2254 moves in a second direction 2282, causing the stroke limiter 2226 to move in the direction of arrow 2284. As such, the arrangement 2252 is operable to rotate the stroke limiter 2226, thereby causing the stroke limiter 2226 to one of extend or retract within the probe 2200 due to threading engagement between the stroke limiter 2226 and the housing 2202.

User input for adjusting a position of the stroke limiter 2226 may be inputted in a manner similar to that described above.

Figure 26:
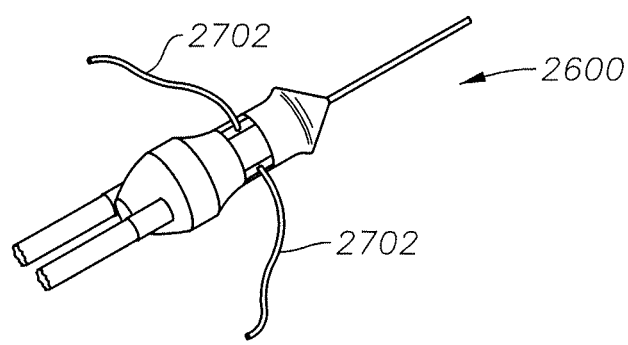
FIGS. 26-32 show another example vitrectomy probe that includes a fluidically-operated stepper motor for adjusting cutter port size.
Figure 27:
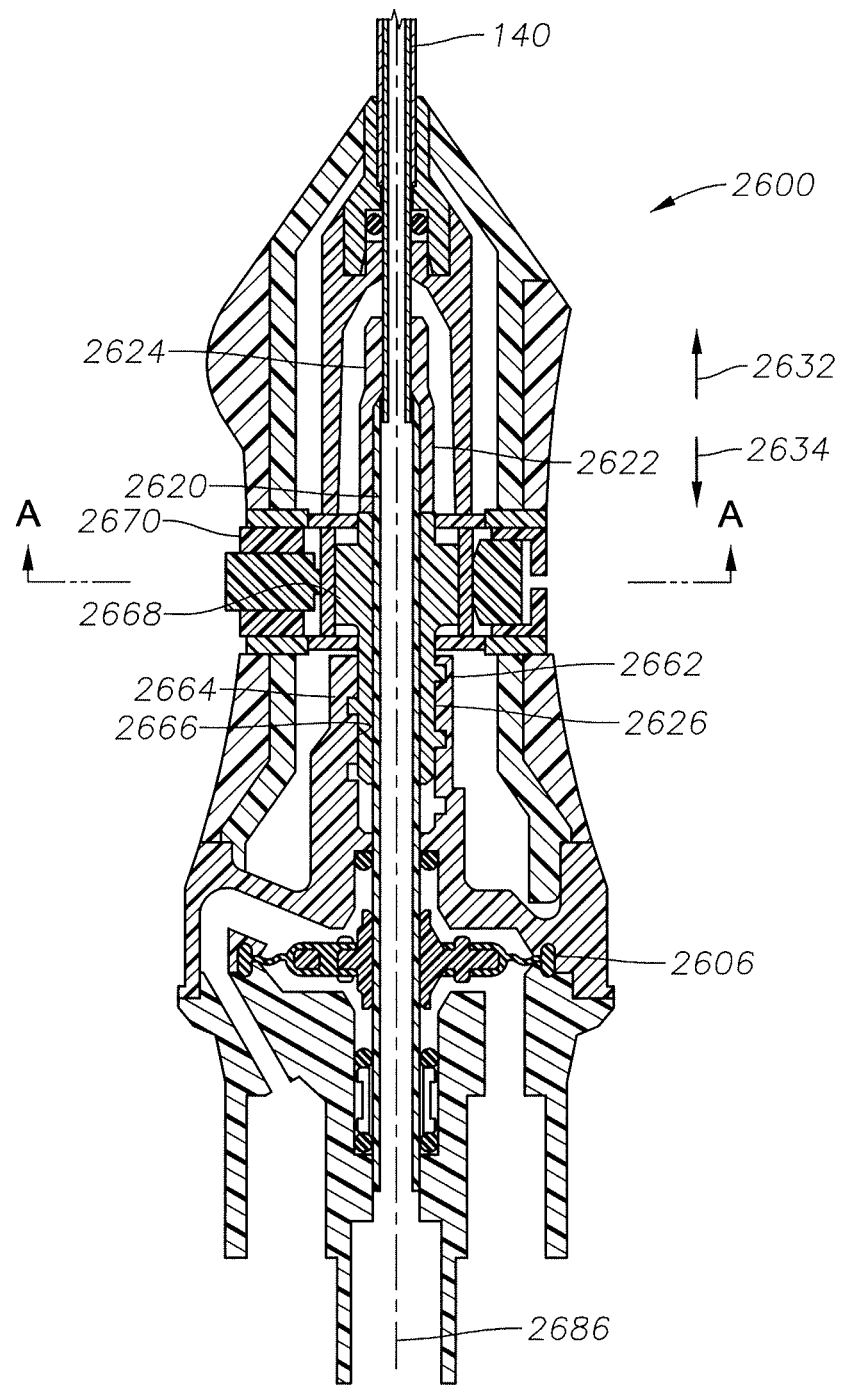

FIGS. 26-27 show another example vitrectomy probe 2600. As discussed below, probe 2600 utilizes a stepper motor 2670 to adjust a position of a stroke limiter 2626. In the example explained below, the stepper motor is a pneumatically operated stepper motor. However, in other implementations, other types of stepper motors could be used. For example, an electrically operated stepper motor may be used. As such, the example probe 2600 described with respect to a pneumatic stepper motor is provided merely as an example and is not intended to be limiting. Accordingly, stepper motors of other types are included within the scope of the present disclosure.

As shown in the cross-sectional view of FIG. 27, the probe 2600 includes an interior assembly 2624, stroke limiter 2626, and a motor 2606 similar to one or more of the motors described herein. The interior assembly 2624 may be coupled to and oscillate with the motor 2606. As also shown, the interior assembly 2624 includes a coupling 2622. However, as explained above, the interior assembly 2624 may have other configurations. For example, the coupling 2622 may be eliminated and the inner cutting member 140 may be coupled directly to tube 2620. Additionally, a collar, similar to that shown in FIG. 10, may be disposed about the tube 2620 to provide a contacting surface that contacts the stroke limiter 2626 to define the size of the port (as shown, for example, in FIGS. 4-8).

The stroke limiter 2626 may be similar to the stroke limiter 960, discussed above. That is, the stroke limiter 2626 may include a threaded surface 2662, and the stroke limiter 2626 may be threadably retained within an interior sleeve 2664. The threaded surface 2662 may cooperatively engage an inner threaded surface 2666 of the interior sleeve 2626. Thus, as the stroke limiter 2626 is rotated in a first direction, the stroke limiter 2626 may move in a direction of arrow 2632. Alternately, the stroke limiter 2626 may move in the direction of arrow 2634 when rotated in a second direction, opposite the first direction. Movement of the stroke limiter 2626 in the direction of arrows 2632 and 2634 acts to decrease or increase a size of the port 120, respectively.

Figure 28:
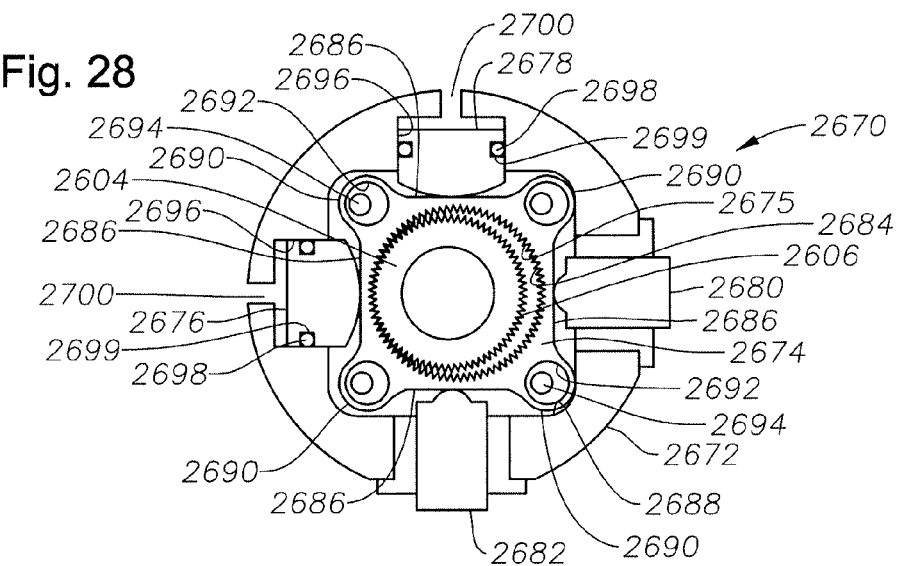

FIG. 28 is a cross-section of the example probe 2600 taken along line A-A in FIG. 27. Referring to FIG. 28, in some implementations, the stepper motor 2670 includes a housing 2672, an eccentric gear 2674, a first piston 2676, a second piston 2678, a first biasing element 2680, and a second biasing element 2682. The eccentric gear 2674 includes an opening 2675 and contacting surfaces 2686. An internal geared surface 2684 is formed on an interior surface defining the opening 2675. The eccentric gear 2674 is disposed within an opening 2688 formed within the housing 2672 and is moveable in the opening 2688 within a plane perpendicular to longitudinal axis 2686. In some instances, the eccentric gear 2674 may have rounded edges 2690. The rounded edges 2690 may contact an interior surface of the opening 2688 to limit an amount of movement of the eccentric gear 2674 therein. Still further, in some instances, the eccentric gear 2674 may include a plurality of openings 2692 that receive posts 2694. The post and opening arrangement may be used to retain the eccentric gear 2672 within the opening 2688 while also providing for movement of the eccentric gear 2674 within the opening 2688.

Pistons 2676, 2678 are slideable within cylinders 2696 formed within the housing 2672. The pistons 2676, 2678 may include seals 2698 received into grooves 2699. The seals 2698 may be similar to other seals described herein and may be operable to prevent and/or substantially reduce the passage of fluid. Fluidic pressure may be introduced into the cylinders 2696 via openings 2700. In some implementations, fluidic pressure may be supplied to the cylinders 2696 via conduits 2702 (shown in FIG. 26). In some instances, the fluidic pressure is pneumatic pressure. In other instances, the fluidic pressure may be hydraulic pressure. Further, as explained above, the stepper motor may be electrically operated.

The stroke limiter 2626 may include an internal drive gear 2604. The internal drive gear 2604 includes a geared surface 2606. The internal drive gear 2604 is received within the opening 2675. The opening 2675 may have a diameter larger than a diameter of the internal drive gear 2604. A portion of the geared surface 2606 of the internal drive gear 2604 engages a portion of the internal geared surface 2684. The teeth defining the geared surfaces 2606 and 2684 are longitudinally arranged. That is, the teeth may be oriented parallel to axis 2686. Thus, as the stroke limiter 2626 is moved in the directions of arrows 2632, 2634 (as described below), the stroke limiter 2626 is able to move relative to the internal gear 2672. User input for adjusting a position of the stroke limiter 1626 may be inputted in a manner similar to that described above.

Figure 29:
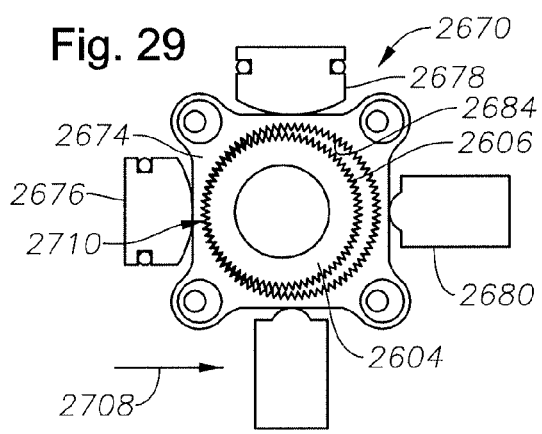

FIGS. 29-32 illustrate operation of the example stepper motor 2670. Referring to FIG. 29, as fluidic pressure is applied to first piston 2676, the piston 2676 overcomes a biasing force applied by the first biasing element 2680 to the eccentric gear 2674, causing the eccentric gear 2674 to be displaced in the direction of arrow 2708. Displacement of the eccentric gear 2674 in the direction of arrow 2708 causes the geared surfaces 2684, 2606 of the eccentric gear 2574 and the internal drive gear 2604, respectively, to engage each other at 2710.

Figure 30:
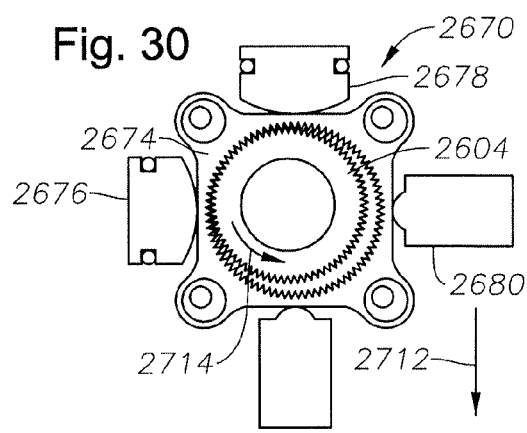
Figure 31:
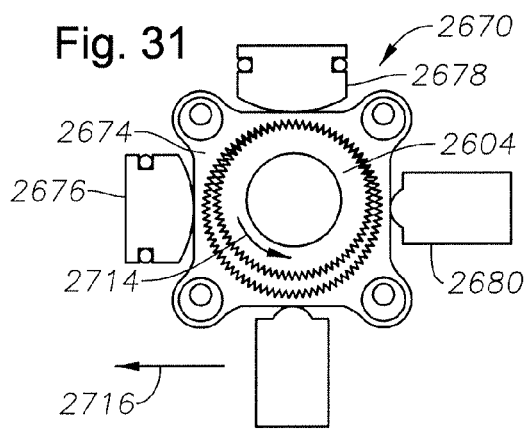
Figure 32:
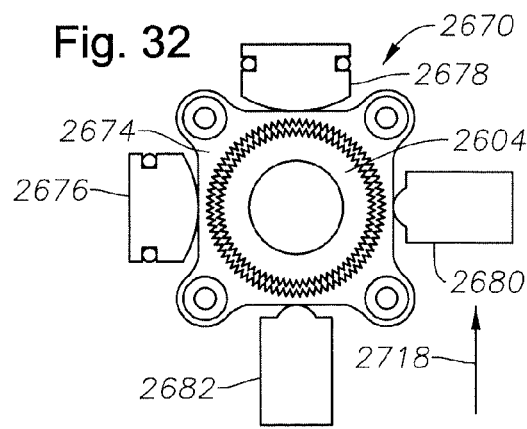

As shown in FIG. 30, as fluidic pressure is applied to the second piston 2678, the eccentric gear 2674 is moved in the direction of arrow 2712 to cause the internal drive gear 2604 to be rotated in the direction of arrow 2714. Referring to FIG. 31, as fluidic pressure is released from the first piston 2676, the eccentric gear 2674 is displaced in the direction of arrow 2716 by the first biasing element 2680, further causing the internal drive gear 2604 to be further rotated in the direction of arrow 2714. Referring to FIG. 32, as fluidic pressure is removed from the second piston 2678, the second biasing element 2682 urges the eccentric gear 2674 in the direction of arrow 2718, such that the eccentric gear 2674 is returned to an initial position.

As a result, the internal drive gear 2684 is rotated a defined amount in the direction of arrow 2714. This process may be repeated to further rotate the internal drive gear 2684 in the direction of arrow 2714 to achieve a desired amount of rotation of the stroke limiter 2726. Alternately, the previously described process may be reversed such that the internal drive gear 2684 (and, hence, the stroke limiter 2626) is rotated in a direction opposite of arrow 2714. As a result, the size of port 120 may be carefully controlled by rotating the stroke limiter 2626 in alternate directions to one of extend or retract the stroke limiter 2626 within the probe 2600. Further, the rate at which the stroke limiter 2626 may also be controlled by the rate at which the first and second pistons 2676, 2678 are actuated. A user may adjust a position of the stroke limiter 2626 by interacting with the probe 2600, a console to which the probe 2600 is coupled, or an input device in a manner similar to that described above.

Still further, in other implementations, the first and second biasing elements 2680, 2682 may be replaced with additional pistons. In such an implementation, application of fluidic pressure to the pistons may be used to control rotation of internal drive gear 2684 in a manner similar to that described above. Thus, in some implementations, the pistons may be utilized to provide a biasing or return force to displace the internal drive gear 2684 in a direction opposite the force of an opposing piston. In still other implementations, three or more fluidically operated pistons may be used to control the rotation of the internal drive gear 2684 and, consequently, the stroke limiter 2626.

Figure 33:
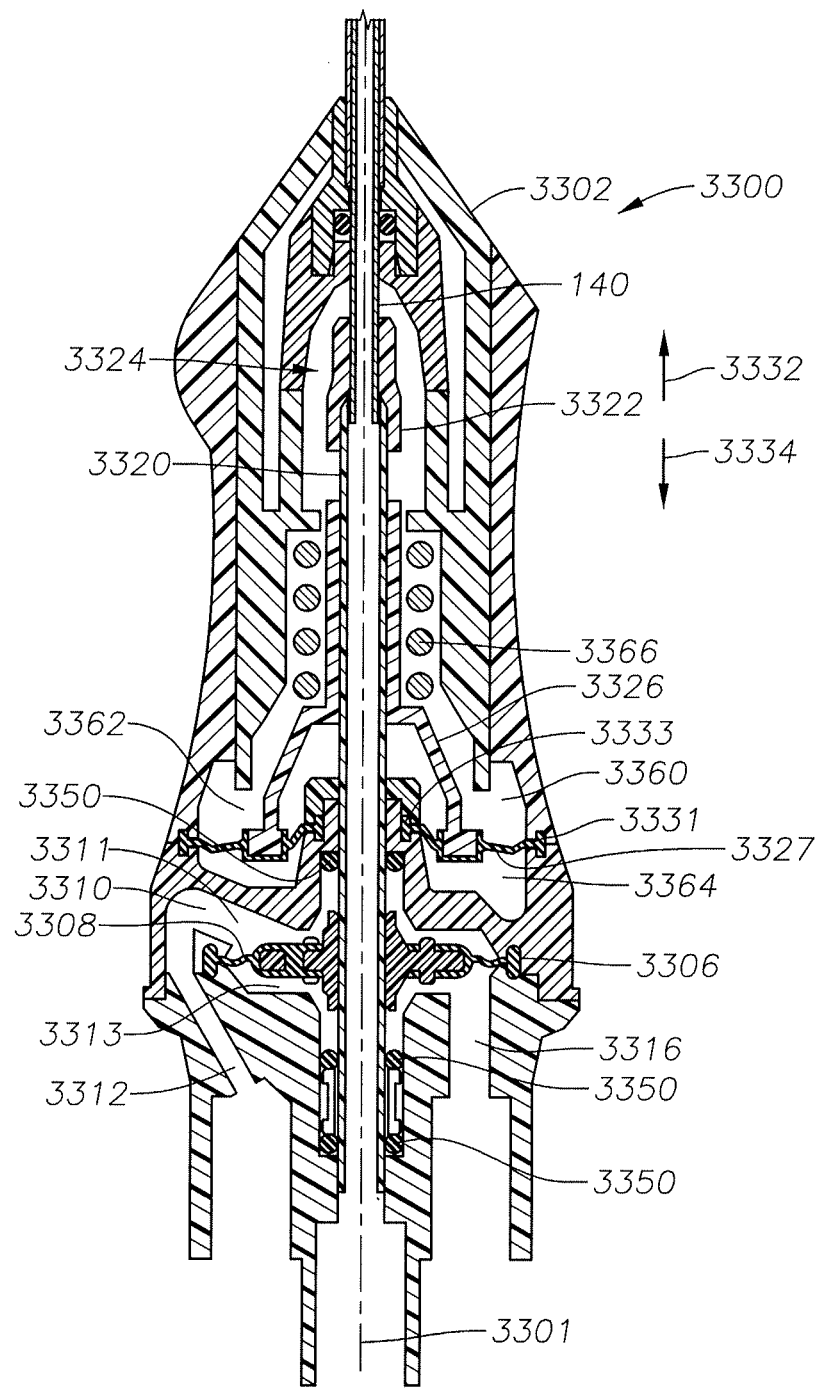
FIGS. 33-34 show another example vitrectomy probe that utilizes fluidic pressure to adjust cutter port size.
Figure 34:
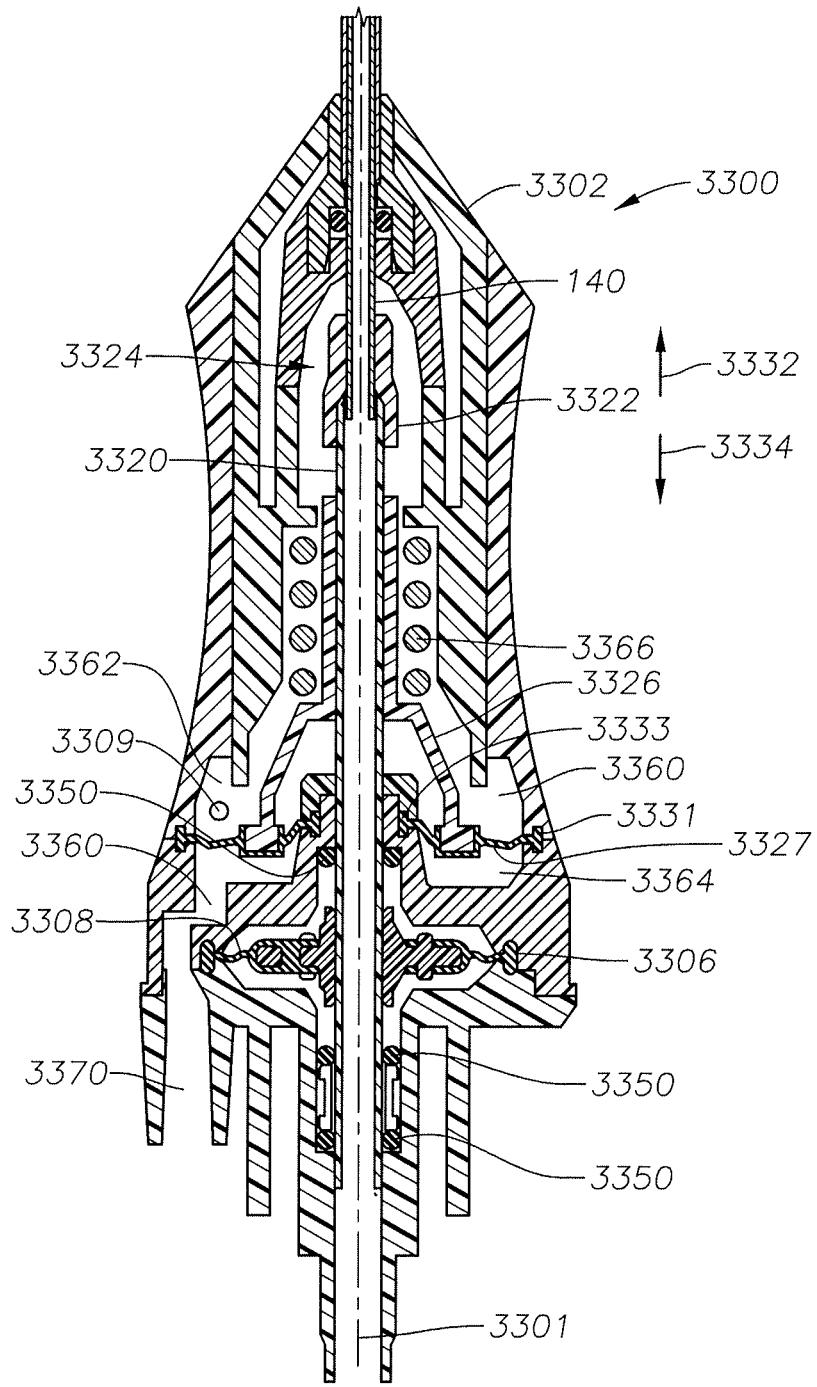

FIGS. 33 and 34 show partial cross-sectional views of another example probe 3300 that utilizes pressurized gas to adjust a position of a stroke limiter. FIG. 34 is a detail cross-sectional view of the example probe 3300 taken along a plane passing through probe 3300 different than that of the plane defining the cross-sectional view shown in FIG. 33. For example, the cross-section shown in FIG. 33 may be approximately 90° offset from the cross-sectional view shown in FIG. 34 taken about axis 3301.

Referring to FIG. 33, the example probe 3300 includes a housing 3302 and an interior assembly 3324. The interior assembly 3324 may be similar to one or more of the other interior assemblies described herein. In the example shown, the interior assembly 3324 includes inner cutting member 140, hollow coupling 3322, and tube 3320. However, the interior assembly 3324 is not so limited and may be configured differently. The interior assembly 3324 may be coupled to a motor 3306 that may operate in a manner similar to one or more of the motors (e.g., motors 906, 1106, 1406, 1606, and 2506), described above. For example, the motor 3306 may include a diaphragm 3308 disposed in a first chamber 3310. The diaphragm 3308 bisects the first chamber 3310 into a first chamber portion 3311 and a second chamber portion 3313. A first passage 3312 communicates with the first chamber portion 3311, and a second passage 3316 communicates with the second chamber portion 3313. Pressurized gas may be alternately applied through the first passage 3312 and the second passage 3316 to oscillate the diaphragm 3308, thereby oscillating the interior assembly 3324.

The probe 3300 may also include a second chamber 3360, a stroke limiter 3326, and a diaphragm 3327. In some instances, the diaphragm 3327 may be coupled to the housing 3302 at an outer periphery 3331 and at an inner periphery 3333. The stroke limiter 3326 may be coupled to the diaphragm 3327 at a location between the outer periphery 3331 and the inner periphery 3333.

The diaphragm 3327 bisects the second chamber 3360 to form a first chamber portion 3362 and a second chamber portion 3364. The diaphragm 3327 reacts to pressure differences between the first chamber portion 3362 and the second chamber portion 3364 to cause the stroke limiter 3326 to move longitudinally relative to the housing 3302. A biasing member 3366 may be disposed in the first chamber portion 3362 between the stroke limiter 3326 and a portion of the housing 3302 or other portion of the probe 3300 stationary relative to the stroke limiter 3326. In some instances, the biasing member 3366 is a spring. The biasing member 3366 provides a biasing force urging the stroke limiter 3326 in a direction of arrow 3334. For example, in some instances, the biasing member 3366 is a coil spring. However, the biasing member 3366 is not so limited and may be any suitable member operable to provide a biasing force to the stroke limiter 3326.

Referring to FIG. 34, pneumatic pressure may be introduced into and released from the second chamber portion 3364 via a passage 3370. Thus, pneumatic pressure may be applied to the diaphragm 3327 via passage 3370 to position stroke limiter 3326 at a desired location. An orifice 3309 may be formed between the first chamber portion 3362 and an exterior of the probe 3300 to provide fluid communication therebewteen. The orifice 3309 allows movement of air into an out of the first chamber portion 3362 as the diaphragm 3327 and stroke limiter 3326 moves within the second chamber 3360. As such, the orifice 3309 prevents formation of a vacuum in the first chamber portion 3362, thereby allowing the stroke limiter 3326 to move responsive to movement of the diaphragm 3327. In other instances, the orifice 3309 may be eliminated, and air in the first chamber portion 3362 may be allowed to enter and escape through gaps formed between one or more components of the probe 3300. Further, pneumatic pressure applied to the second chamber portion 3364 to position stroke limiter 3326 may be applied independently of the pneumatic pressure utilized to operate motor 3306.

Pneumatic pressure acts on the diaphragm 3327, applying a force on the stroke limiter 3326 against a biasing force of the spring 3366. The stroke limiter 3326 may be displaced when the applied force on the stroke limiter 3326 exceeds the biasing force applied by the spring 3366. A spring rate of the spring 3366 may be any desired spring rate. For example, the spring rate of spring 3366 may be selected to cause the stroke limiter to displace in the direction of arrow 3332 at a desired pneumatic pressure.

In the illustrated example, movement of the interior assembly 3324 and, hence, the inner cutting member 140 is limited by contact between hollow coupling 3322 and the stroke limiter 3326. The stroke of the inner cutting member 140 and, consequently, the port size 120 is reduced as the stroke limiter 3326 is moved in the direction of arrow 3332. Conversely, the stroke of the inner cutting member 140 and the port size 120 is increased by movement of the stroke limiter 3325 in the direction of arrow 3334.

As the pneumatic pressure decreases in the second chamber portion 3364, the spring force from spring 3366 overcomes the force applied by the pneumatic pressure acting on the diaphragm 3327, causing the stroke limiter 3326 to move in the direction of arrow 3334. Therefore, the position of the stroke limiter 3326 may be adjusted to a desired position based on a pressure of the gas. Thus, for a given pneumatic pressure, the stroke limiter 3326 may displace a given amount and remain substantially at that position. A higher gas pressure may displace the stroke limiter 3326 a larger amount in the direction of arrow 3332. Similarly, a lower gas pressure may cause the stroke limiter 3326 to move in the direction of arrow 3334 a lesser amount. Thus, the position of the stroke limiter 3326 and, consequently, the size of the cutter port, may be controlled based on the pressure of the gas.

The probe 3300 may also include one or more seals 3350. Although three seals 3350 are shown, more or fewer seals 3350 may be used. In still other instances, seals 3350 may be eliminated. The seals 3350 may provide an air-tight or substantially air-tight seal.

Thus, in operation, a pneumatic pressure corresponding to a desired cutter port size may be introduced into and maintained in the second chamber portion 3364 via passage 3370 to maintain a desired position of the stroke limiter 3326. The spring 3366 may provide a bias force on the stroke limiter 3326. The pneumatic pressure applied to the second chamber portion 3364 may be altered when a change in position of the stroke limiter 3326 is desired. For example, the applied pneumatic pressure may be increased to reduce the cutter port size, for example, by moving stroke limiter 3326 in the direction of arrow 3332. Alternately, the applied pneumatic pressure may be decreased to increase the cutter port size, for example, by moving the stroke limiter 3326 in the direction of arrow 3334. Still further, in some instances, no pneumatic pressure may be applied to the second chamber portion 3364, providing for the port to open a maximum amount. Similar to the other probes described herein, a user may adjust a position of the stroke limiter 3326 and, hence, the port size, for example, by interacting with a control provided on one or more of the probe 3300, the surgical console to which the probe 3300 is coupled, or a input device, such as an input device coupled to the surgical console.

Figure 39:
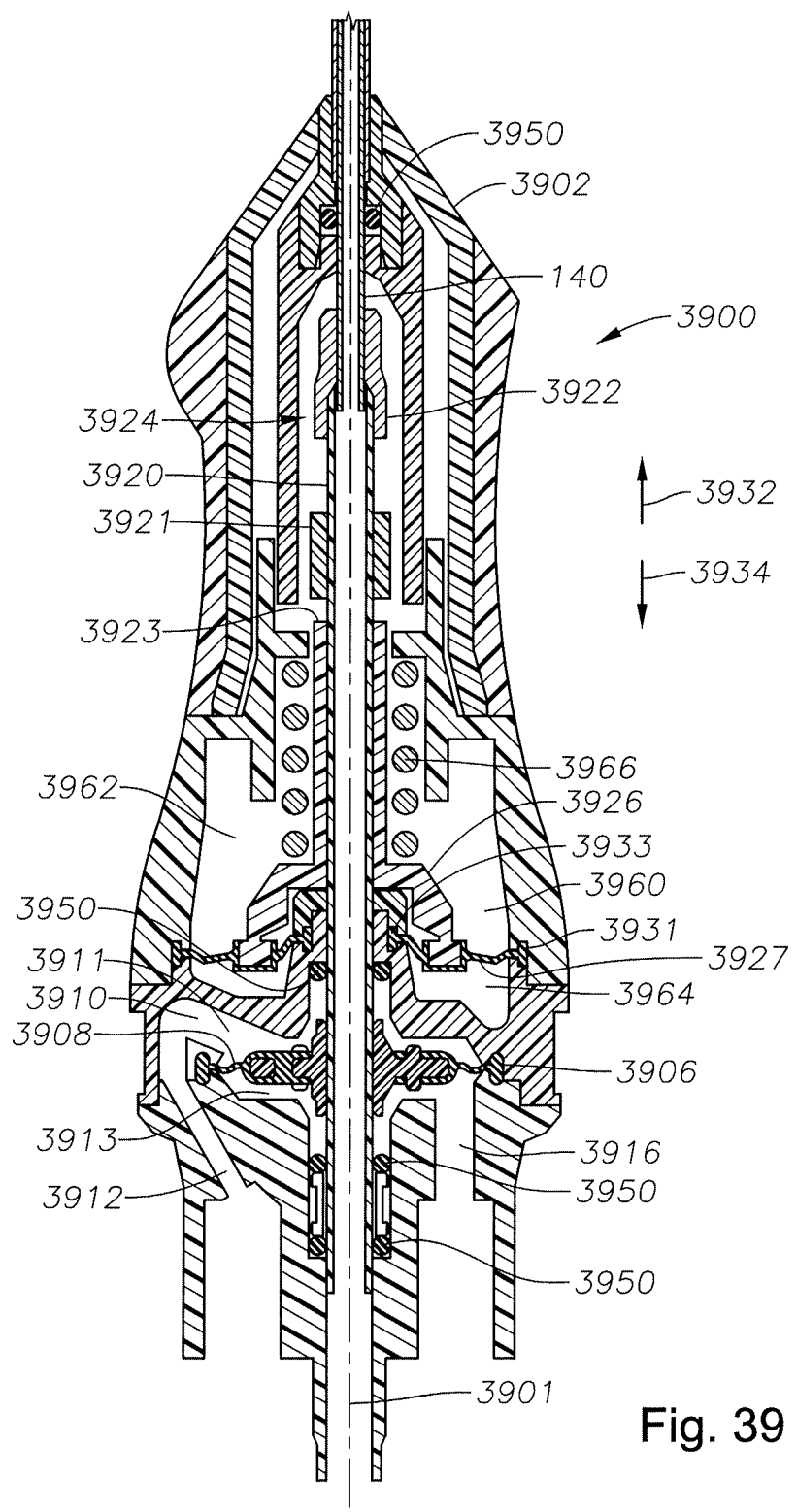

FIGS. 39 and 40 show another example probe 3900. FIGS. 39 and 40 show cross-sectional views of the example probe 3900 along different planes. For example, the cross-sectional view shown in FIGS. 39 and 40 may be 90 degrees offset from each other about the longitudinal axis 3901.

The probe 3900 may include a housing 3902 and an interior assembly 3924. The interior assembly 3925 may include an inner cutting member 140, tube 3920, and hollow coupling 3922. A collar 3921 may also be coupled to the tube 3920. The collar 3321 may interact with the stroke limiter 3926 (such as end surface 3923 of the stroke limiter 3926) to limit a stroke amount of the interior assembly 3924 and, hence, the inner cutting member 140. The interior assembly 3925 may be coupled to a motor 3906 that may operate in a manner similar to one or more of the motors (e.g., motors 906, 1106, 1406, 1606, and 2506), described above. For example, the motor 3906 may include a diaphragm 3908 disposed in a first chamber 3910. The diaphragm 3908 bisects the first chamber 3910 into a first chamber portion 3911 and a second chamber portion 3913. A first passage 3912 communicates with the first chamber portion 3911, and a second passage 3916 communicates with the second chamber portion 3913. Pressurized gas may be alternately applied through the first passage 3912 and the second passage 3916 to oscillate the diaphragm 3908, thereby oscillating the interior assembly 3925.

The probe 3900 may also include a second chamber 3960, the stroke limiter 3926, and a diaphragm 3927. In some instances, the diaphragm 3927 may be coupled to the housing 3902 at an outer periphery 3931 and at an inner periphery 3933. The stroke limiter 3926 may be coupled to the diaphragm 3927 at a location between the outer periphery 3931 and the inner periphery 3933.

The diaphragm 3927 bisects the second chamber 3960 to form a first chamber portion 3962 and a second chamber portion 3964. The diaphragm 3927 reacts to pressure differences between the first chamber portion 3962 and the second chamber portion 3964 to cause the stroke limiter 3326 to move longitudinally relative to the housing 3902. A biasing member 3966 may be disposed in the first chamber portion 3962 between the stroke limiter 3926 and a portion of the housing 3902 or other portion of the probe 3900 stationary relative to the stroke limiter 3926. In some instances, the biasing member 3966 is a spring. The biasing member 3966 provides a biasing force urging the stroke limiter 3926 in a direction of arrow 3934. For example, in some instances, the biasing member 3966 is a coil spring. However, the biasing member 3966 is not so limited and may be any suitable member operable to provide a biasing force to the stroke limiter 3926.

Referring to FIG. 40, pneumatic pressure may be introduced into and released from the second chamber portion 3964 via a passage 3970. Thus, pneumatic pressure may be applied to the diaphragm 3927 via passage 3970 to position stroke limiter 3926 at a desired location. The probe 3900 may include an orifice 3909, similar to 3309, formed between the first chamber portion 3962 and an exterior of the probe 3900 to provide fluid communication therebewteen. In other instances, the orifice 3909 may be eliminated, and air may be allowed to enter and exit the second chamber portion 3960 through one or more gaps formed between one or more components of the probe 3900. Further, pneumatic pressure applied to the second chamber portion 3964 to position stroke limiter 3926 may be applied independently of the pneumatic pressure utilized to operate motor 3906.

Probe 3900 may also include seals 3950 at one or more of the locations shown. Although four seals 3950 are shown, more or fewer seals 3950 may be used. In still other instances, seals 3950 may be eliminated. The seals 3950 may provide an air-tight or substantially air-tight seal.

The probe 3900 may operate in a manner similar to the probe 3300, described above. Thus, pneumatic pressure corresponding to a desired cutter port size may be introduced into and maintained in the second chamber portion 3964 via passage 3970 to maintain a desired position of the stroke limiter 3926. The spring 3966 may provide a bias force on the stroke limiter 3926. The pneumatic pressure applied to the second chamber portion 3964 may be altered when a change in position of the stroke limiter 3926 is desired. For example, the applied pneumatic pressure may be increased to reduce the cutter port size, for example, by moving stroke limiter 3926 in the direction of arrow 3932. Alternately, the applied pneumatic pressure may be decreased to increase the cutter port size, for example, by moving the stroke limiter 3926 in the direction of arrow 3934. Still further, in some instances, no pneumatic pressure may be applied to the second chamber portion 3964, providing for the port to open a maximum amount. Similar to the other probes described herein, a user may adjust a position of the stroke limiter 3926 and, hence, the port size, for example, by interacting with a control provided on one or more of the probe 3900, the surgical console to which the probe 3900 is coupled, or a input device, such as an input device coupled to the surgical console.

Figures 35, 36:
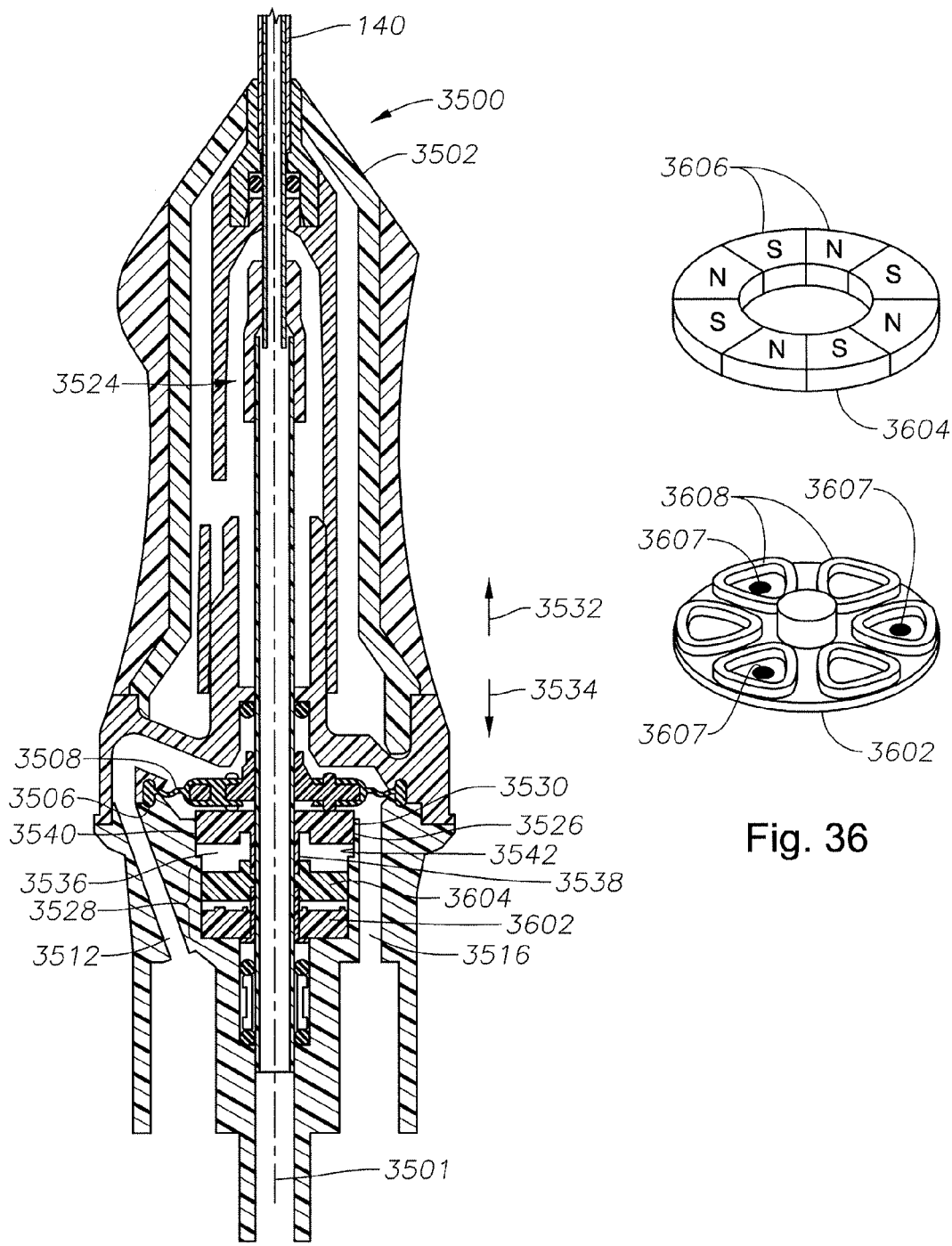
FIGS. 35-36 show another example vitrectomy probe that includes a pancake motor for adjusting cutter port size.

FIG. 35 shows another example probe 3500 in which a stroke limiter 3526 includes a pancake motor 3528. Similar to one or more of the probes described above, the probe 3500 includes a motor 3506. The motor 3506 may include a diaphragm 3508 for oscillating the interior assembly 3525. The diaphragm 3508 may be actuated in a manner similar to that described above. For example, the diaphragm 3508 may be oscillated by alternating application of pneumatic pressure to the diaphragm 3508 via passages 3512 and 3516. However, the motor 3506 may be any device operable to generate oscillation.

The stroke limiter 3526 includes the pancake motor 3528 and a stop screw 3530. The pancake motor 3528 is operable to adjust a location of the stop screw 3530 relative to the diaphragm 3508. This change alters the location at which the diaphragm 3508 contacts the stop screw 3530, thereby altering the cutter port size. Movement of the stroke limiter 3526 to adjust the port size may be altered as desired, such as by a user. Example users may include a surgeon, physician, or other personnel.

As shown in FIG. 36, a pancake motor 3600 is any of a group of motors that have a flat, substantially disk-shaped stator 3602 and rotor 3604. As shown in the illustrated example, the rotor 3604 includes a plurality of wedge-shaped magnets 3606 arranged in a circular fashion. Opposing magnets 3606 have opposite polarity. The stator 3602 includes a plurality of stator coils 3608 that are configured to overlay the plurality of magnets 3606. The stator 3602 may also include one or more motion detection sensors 3607. For example, in some instances, the one or more sensors 3607 may be hall effect sensors. The hall effect sensors are operable to detect whether the rotor 3604 is rotating and, if so, a direction of rotation of the rotor 3604. As shown, a sensor 3607 is disposed within a region defined by a stator coil 3608. Further, FIG. 36 shows that a sensor 3607 may be disposed within this region of every other stator coil 3607. However, the scope is not so limited. Rather, any sensor operable to determine rotation and/or direction of rotation may be used. Further, any number of sensors may be used.

When assembled, the stator 3602 and rotor 3604 are stacked in a coaxial arrangement. The rotor 3604 is rotated in a step-wise manner as current is selectively passed through the stator coils 3608. Further, the direction of rotation of the rotor 3604 may be selected based on the direction in which current is passed through the stator coils 3608.

Returning to FIG. 35, the pancake motor 3528 is disposed in a cavity 3536 and may be arranged in a coaxial arrangement with the interior assembly 3524 about longitudinal axis 3501. In some implementations, the stop screw 3530 may be slidingly engaged with the rotor 3604 of the pancake motor 3528 by a sleeve 3538 coupled to an inner perimeter of the stop screw 3530. Thus, the stop screw 3530 is operable to rotate with the stator 3604 while also being slideable relative to the rotor 3604 along the longitudinal axis 3501. An outer perimeter surface 3540 of the stop screw 3530 matingly engages an interior surface 3542 of the housing 3502, such as by mating threads. Thus, as the stop screw 3530 is rotated by the rotor 3604, the mating threads of the outer perimeter surface 3540 and interior surface 3542 cooperate to cause the stop screw 3530 to move in the direction of arrow 3532 or 3534, depending on the direction of rotation of the rotor 3604.

Movement of the stop screw 3530 in the direction of arrow 3532 places the stop screw 3530 in closer proximity to the diaphragm 3508. Accordingly, smaller displacements of the diaphragm 3508 in the direction of arrow 3534 cause the diaphragm 3508 to engage the stop screw, resulting in a reduced port size. Alternately, movement of stop screw 3530 in the direction of arrow 3534 results in a larger displacement of the diaphragm 3508 in the direction of arrow 3534, thereby increasing the port size. A user may adjust a position of the stop screw 3530, for example, in a manner similar to that described above.

Figure 37:
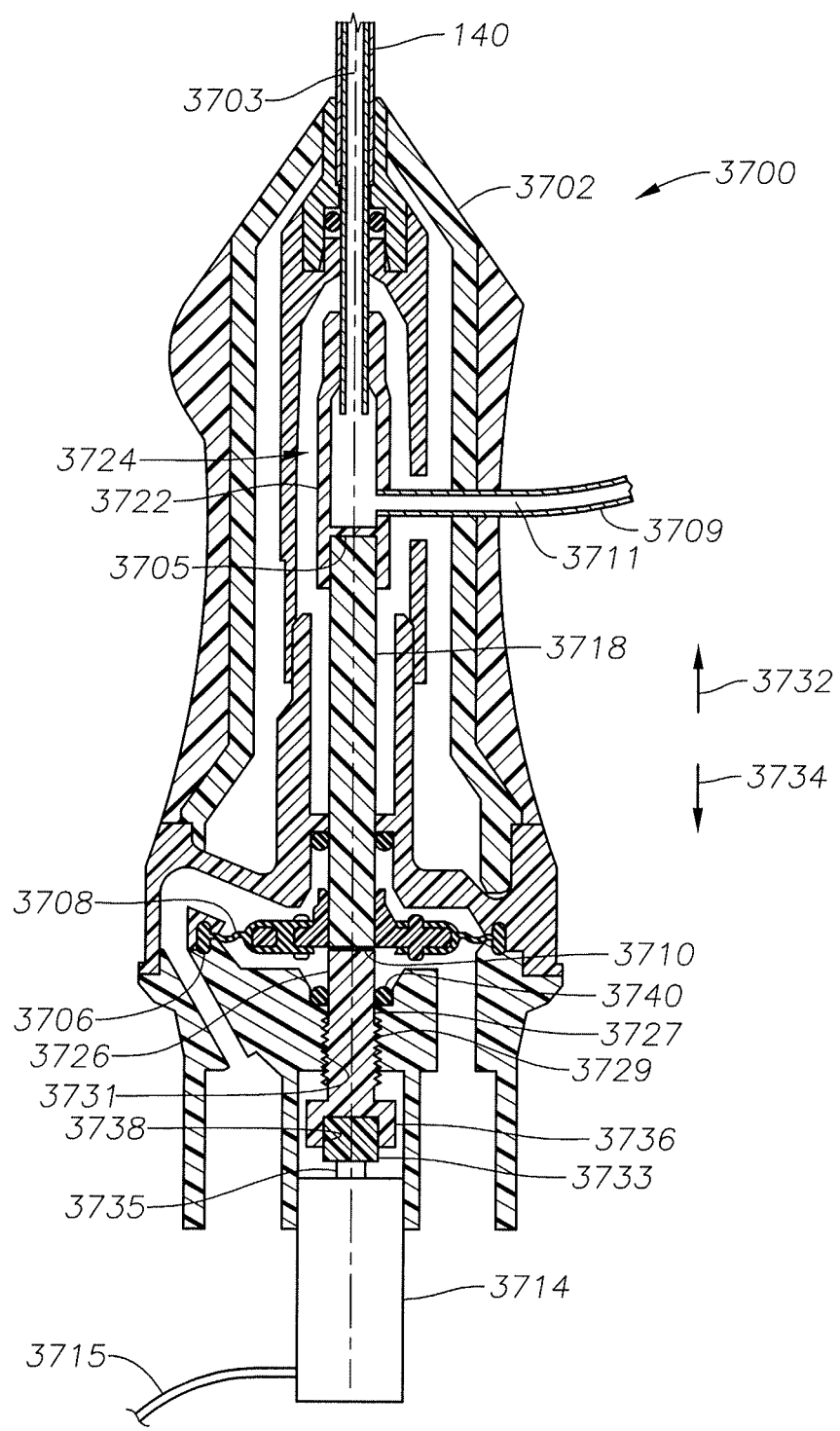
FIG. 37 shows another example vitrectomy probe for adjusting cutter port size utilizing a motor mounted to the probe.

FIG. 37 shows a cross-sectional view of a portion of another example probe 3700. The probe 3700 may be similar to one or more other of the probes described herein and include a housing 3702 and a motor 3706. In some instances, the motor 3706 may include a diaphragm 3708 that may be similar to one or more of the other diaphragms described herein. The diaphragm 3708 may be oscillated in response to alternating application of pneumatic pressure. However, the motor 3706 may not include a diaphragm. Rather, the motor 3706 may be any device operable to generate an oscillation.

The probe 3700 may also include an interior assembly 3724. The interior assembly 3724 may include an extension 3718, a coupler 3722, and an inner cutting member 140. The inner cutting member 140 defines a passage 3703 and has a terminal end 3705. The passage 3703 is in communication with a passage 3711 formed in a conduit 3709. The passage 3703 and passage 3711 cooperate to pass materials, such as tissues and fluids, out of the eye. The components of the interior assembly 3724 are coupled so as to move as a unitary piece. The interior assembly 3724 is coupled to the diaphragm 3708 via the extension 3718.

The probe 3700 also includes a stroke limiter 3726. The stroke limiter 3726 extends through a bore 3727 formed in the housing 3702 of the probe 3700. The stroke limiter 3726 may include a threaded exterior surface 3729 adapted to matingly engage a corresponding threaded surface 3731 formed on interior surface of the bore 3727. In some instances, a seal 3740 may also be included, for example, to form a seal between the stroke limiter 3726 and the housing 3702.

The probe 3700 may also include a motor 3714. Electrical connections may be provided to the motor 3714 via cable 3715. The motor 3714 may include a coupler 3733 coupled to a shaft 3735 thereof. The coupler 3733 is operable to couple to an end 3736 of the stroke limiter 3726. As such, as the shaft 3735 of the motor 3714 is rotated, the stroke limiter 3726 is also rotated. In some instances, the coupler 3733 is received into a recess 3738 formed in the end 3736 of the stroke limiter 3726. In some instances, the recess 3738 and the coupler 3733 may form a splined connection. Thus, with a splined connection, the stroke limiter 3726 is operable to both rotate with or in response to the coupler 3733 while also being able to move in the direction of arrows 3732, 3734 relative to the coupler 3733. However, the coupler 3733 may be coupled to the stroke limiter 3726 in any other manner that is operable to permit the stroke limiter 3726 rotate with or in response to the coupler 3733 or shaft 3735 while also permitting the stroke limiter 3726 to move relative to the coupler 3733 and/or shaft 3735 in the direction of arrows 3732, 3734. In still other instances, the coupler 3733 may be eliminated, and the stroke limiter 3726 may be coupled to the shaft 3735, such as via a splined connection or any other type of connection described above in which the stroke limiter 3726 is operable to rotate with or in response to the shaft 3735 while also being operable to move relative to the shaft 3735 in the direction of arrows 3732, 3734.

In some instances, the probe 3700 may also include a gear set disposed between the stroke limiter 3726 and the motor 3714. For example, in some implementations, a 6 to 1 ratio gear set may be used in combination with the motor 3714. A gear set may be utilized to modulate an amount of rotation of the stroke limiter 3726 relative to the motor 3714. That is, the gear set may be used to reduce or increase an amount of rotation of the stroke limiter 3726 in relation to the rotation of the motor 3714.

In operation, according to some implementations, as the motor 3714 rotates the shaft 3735 in a first direction, the stroke limiter 3726 is also rotated. As the stroke limiter 3726 is rotated in the first direction, the stroke limiter 3726 may be extended (i.e., moved in the direction of arrow 3732) as a result of the threaded connection between the stroke limiter 3726 and the bore 3727. As the stroke limiter 3726 is moved in the direction of arrow 3732, a location where an end surface 3710 of the stroke limiter 3726 contacts a portion of the interior assembly 3724 is changed. For example, in some instances, the stroke limiter 3726 may contact an end of the extension 3718. In other instances, the end surface 3710 of the stroke limiter 3726 may contact a portion of the diaphragm 3708. Thus, a change in position of the stroke limiter 3726 alters a location at which the stroke limiter 3726 contacts a portion of the interior assembly 3724 or diaphragm 3718. Consequently, the stroke of the interior assembly 3724 in the direction of arrow 3734 is decreased, resulting in a reduced port size of the probe 3700.

Alternatively, as the shaft 3735 is rotated in a second direction, opposite the first direction, the stroke limiter 3726 is also rotated in the second direction. Rotation of the stroke limiter 3726 in the second direction causes the stroke limiter 3726 to be retracted (i.e., moved in the direction of arrow 3734). Consequently, the stroke of the interior assembly 3724 in the direction of arrow 3734 is increased, thereby increasing a port size of the probe 3700. Thus, the stroke limiter 3726 may be extended or retracted to control a port size of the probe 3700.

In still other implementations, rotation of the shaft 3735 in the first direction may cause rotation of the stroke limiter 3726 in an opposite direction. For example, a gear set, such as the gear set of a type discussed above, may be disposed between the shaft 3735 and the stroke limiter 3726 such that rotation of the shaft 3735 in one direction results in rotation of the stroke limiter 3726 in an opposite direction.

In some instance, the cable 3715 may be coupled to a surgical console. Also, in some instances, the motor 3714 may be a stepper motor. For example, in some implementations, the motor 3714 may be an ADM 0620 series stepper motor produced by MicroMo Electronics of 14881 Evergreen Avenue, Clearwater, Fla. However, other types of motors or rotary devices may be used. For example, a mechanically- or fluidically-actuated device may be used to impart rotation. Still other rotary devices may also be used.

Altering a location of the stroke limiter 3726 alters the location at which the extension 3718 contacts the stroke limiter 3712, thereby altering the port size. Similar to the other probes described herein, a user, such as, for example, a physician, may adjust the port size one or more times before, during, or after a surgical procedure. The user may adjust the port size by interacting with a control that may be provided on one or more of the probe 3700, a surgical console coupled to the probe 3700, or on a peripheral device, such as a touch screen, button, slider, footswitch, or other input device, coupled to the surgical console. Signals and/or power for operating the stroke limiter 3712 may be supplied to the probe 3700 via cable 3715. Further, user input for one or more of the other example probes described herein may be implemented in a manner similar to that described above.

Figure 38:
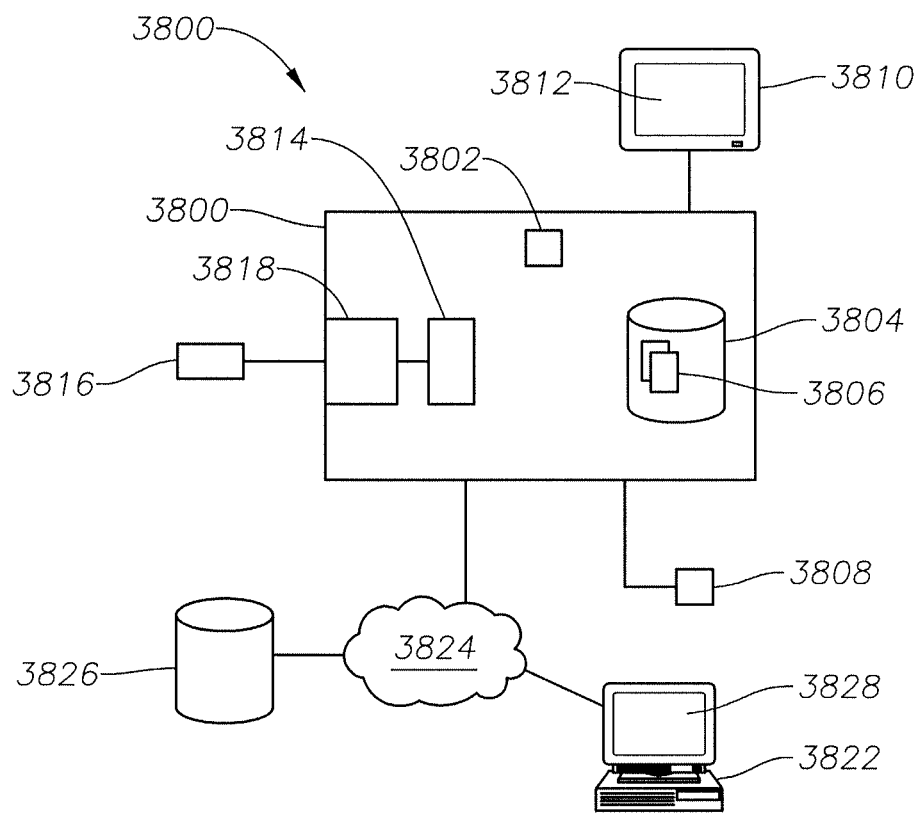
FIG. 38 is a schematic view of an example console for use with a vitrectomy probe having a user-adjustable cutter port size.

FIG. 38 shows a schematic view of an example console 3800 that may be used with one or more of the vitrectomy probes described herein. Consoles 10 may be similar to the console 3800 described herein. An example vitrectomy probe 3816 is shown coupled to the console 3800. The example vitrectomy probe 3816 may be representative of any of the example vitrectomy probes described herein. The console 3800 may be used to provide power to the probe 3816. In some instances, the power provided by the console 3800 may be pneumatic power. In other instances, the power may be electrical power. In still other instances, the power may be hydraulic power. However, in still other instances, the console 3800 may provide any suitable power to the probe 3816 for operation thereof. The console 3800 may also be operable to monitor and/or control other aspects of a surgical procedure for which the console 3800 may be used. For example, the console 3800 may be operable to control an infusion rate of fluid to a surgical site, aspiration of fluid from the surgical site, as well as to monitor one or more patient vital signs.

The console 3800 may include a processor 3802, memory 3804, and one or more applications, including vitrectomy probe application 3806. The console 3800 may also include one or more input devices 3808, and one or more output devices, such as a display 3810. The display 3810 may display a graphical user interface or application interface (collectively referred to as "GUI 3812"), discussed in more detail below. A user may interface with the GUI 3812 to interact with one or more features of the console 3800. The one or more input devices 3808 may include a keypad, a touch screen, a mouse, a foot-operated input device (e.g., a footswitch), or any other desired input device.

Additionally, the console 3800 may include an operations portion 3814. In some instances, the operations portion 3814 may include a power source for a vitrectomy probe, aspiration components, as well as one or more sensors, pumps, valves, and/or other components for operating a vitrectomy probe 3816. The vitrectomy probe 3816 may be coupled to the operations portion 3814 of the console 3800 via an interface panel 3818.

Memory 3804 may include any memory or module and may take the form of volatile or non-volatile memory including, without limitation, magnetic media, optical media, random access memory (RAM), read-only memory (ROM), removable media, or any other suitable local or remote memory component. Memory 3804 may contain, among other items, the vitrectomy probe application 3806. The vitrectomy probe application 3806 may provide instructions for operating aspects of the vitrectomy probe 3816, such as the port size in the probe's 3816 cutter, cutter speed, duty cycle, cutter pulsing configuration, etc.

Memory 3804 may also store classes, frameworks, applications, backup data, jobs, or other information that includes any parameters, variables, algorithms, instructions, rules, or references thereto. Memory 3804 may also include other types of data, such as environment and/or application description data, application data for one or more applications, as well as data involving virtual private network (VPN) applications or services, firewall policies, a security or access log, print or other reporting files, HyperText Markup Language (HTML) files or templates, related or unrelated software applications or sub-systems, and others. Consequently, memory 3804 may also be considered a repository of data, such as a local data repository from one or more applications, such as vitrectomy probe application 3806. Memory 3804 may also include data that can be utilized by one or more applications, such as the vitrectomy probe application 3806.

Application 3806 may include a program or group of programs containing instructions operable to utilize received data, such as in one or more algorithms, and to determine a result or output. The determined results may be used to affect an aspect of the console 3800. The application 3806 may include instructions for controlling aspects of the vitrectomy probe 3816. For example, the application 3806 may include instructions for controlling a port size of the cutter of the vitrectomy probe 3816. For example, the application 3806 may determine one or more adjustments to the operations portion 3814. In some instances, the application 3806 may determine a port size based on input received from input device 3808. The adjustments may be implemented by one or more transmitted control signals to one or more components of console 3800, such as the operations portion 3814. While an example console 3800 is shown, other implementations of the console 3800 may include more, fewer, or different components than those shown.

Figure 20:
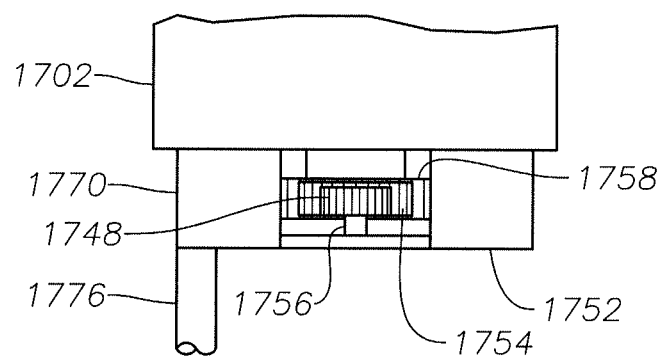
Figure 21:
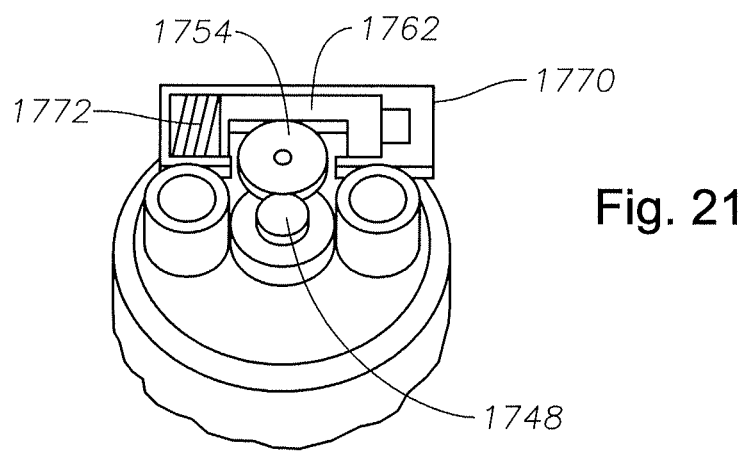
FIGS. 21-23 show another example vitrectomy probe that includes a rack and pinion device for adjusting cutter port size.

Processor 3802 executes instructions and manipulates data to perform the operations of the console 3800, e.g., computational and logic operations, and may be, for example, a central processing unit (CPU), a blade, an application specific integrated circuit (ASIC), or a field-programmable gate array (FPGA). Although FIG. 20 illustrates a single processor 3802 in console 3800, multiple processors 3802 may be used according to particular needs and reference to processor 3802 is meant to include multiple processors 3802 where applicable. For example, the processor 3802 may be adapted for receiving data from various components of the console 3800 and/or devices coupled thereto, process the received data, and transmit data to one or more of the components of the console 3800 and/or devices coupled thereto in response. In the illustrated embodiment, processor 3802 executes vitrectomy probe application 3806.

Further, the processor 3802 may transmit control signals to or receive signals from one or more components coupled thereto. For example, the processor 3802 may transmit control signals in response to received data. In some implementations, for example, the processor 3802 may execute the application 3806 and transmit control signals to the operations portion 3814 in response thereto.

The display 3810 displays information to a user, such as a medical practitioner. In some instances, the display 3810 may be a monitor for visually displaying information. In some instances, the display 3810 may operate both as a display and an input device. For example, the display 3810 may be a touch sensitive display in which a touch by a user or other contact with the display produces an input to the console 3800. The display 3810 may present information to the user via the GUI 3812.

GUI 3812 may include a graphical user interface operable to allow the user to interface with the console 3800 for any suitable purpose, such as viewing application or other system information. For example, GUI 3812 could provide information associated with a medical procedure, including detailed information related to a vitreoretinal surgical procedure and/or operational aspects of the vitrectomy probe 3816.

Generally, GUI 3812 may provide the user with an efficient and user-friendly presentation of information received by, provided by, or communicated within console 3800. GUI 3812 may include a plurality of customizable frames or views having interactive fields, pull-down lists, and buttons operated by the user. GUI 3812 may also present a plurality of portals or dashboards. For example, GUI 3812 may display an interface that allows users to input and define parameters associated with the vitrectomy probe 3816. It should be understood that the term graphical user interface may be used in the singular or in the plural to describe one or more graphical user interfaces and each of the displays of a particular graphical user interface. Indeed, reference to GUI 3812 may indicate a reference to the front-end or a component of application 3806 without departing from the scope of this disclosure. Therefore, GUI 3812 contemplates any graphical user interface. For example, in some instances, the GUI 3812 may include a generic web browser for inputting data and efficiently present the results to a user. In other instances, the GUI 3812 may include a custom or customizable interface for displaying and/or interacting with the various features of the application 3806 or other system services.

In some implementations, the console 3800 may be in communication with one or more local or remote computers, such as computer 3822, over a network 3824. Network 3824 facilitates wireless or wireline communication between console 3800 and any other local or remote computer, such as computer 3822. For example, medical practitioners may use the computer 3822 to interact with configurations, settings, and/or other aspects associated with operation of the console 3800, including the services associated with the application 3806. Network 3824 may be all or a portion of an enterprise or secured network. In another example, network 3824 may be a VPN merely between console 3800 and computer 3822 across wireline or wireless link. Such an example wireless link may be via 802.11a, 802.11b, 802.11g, 802.20, WiMax, ZigBee, Ultra-Wideband and many others. While illustrated as a single or continuous network, network 3824 may be logically divided into various sub-nets or virtual networks without departing from the scope of this disclosure, so long as at least a portion of network 3824 may facilitate communications among console 3800, computer 3822, and/or other devices.

For example, console 3800 may be communicably coupled to a repository 3826 through one sub-net while communicably coupled to computer 3822 through another. In other words, network 3824 encompasses any internal or external network, networks, sub-network, or combination thereof operable to facilitate communications between various computing components. Network 3824 may communicate, for example, Internet Protocol (IP) packets, Frame Relay frames, Asynchronous Transfer Mode (ATM) cells, voice, video, data, and other suitable information between network addresses (collectively or interchangeably referred to as "information"). Network 3824 may include one or more local area networks (LANs), radio access networks (RANs), metropolitan area networks (MANs), wide area networks (WANs), all or a portion of the global computer network known as the Internet, and/or any other communication system or systems at one or more locations. In certain embodiments, network 3824 may be a secure network accessible to users via certain local or remote computer 3822.

Computer 3822 may be any computing device operable to connect or communicate with console 3800 or network 3824 using any communication link. In some instances, computer 3822 may include an electronic computing device operable to receive, transmit, process, and store data, such as any appropriate data associated with console 3800. Computer 3822 may also include or execute a GUI 3828. GUI 3828 may similar to GUI 3812. It will be understood that there may be any number of computers 3822 communicably coupled to console 3800. Moreover, for ease of illustration, computer 3822 is described in terms of being used by one user. But this disclosure contemplates that many users may use one computer or that one user may use multiple computers.

As used in this disclosure, computer 3822 is intended to encompass a personal computer, touch screen terminal, workstation, network computer, kiosk, wireless data port, smart phone, personal data assistant (PDA), one or more processors within these or other devices, or any other suitable processing device. For example, computer 3822 may be a PDA operable to wirelessly connect with an external or unsecured network. In another example, computer 3822 may be a laptop computer that includes an input device, such as a keypad, touch screen, mouse, or other device that can accept information, and an output device that conveys information associated with the operation of console 3800 or computer 3822, including digital data, visual information, or user interface, such as GUI 3828. Both input devices and output devices may include fixed or removable storage media such as a magnetic computer disk, CD-ROM, or other suitable media to both receive input from and provide output to users of computer 3822 through, for example, a display.

As explained above, application 3806 may include instructions for controlling aspects of the vitrectomy probe 3816. Example aspects may include cutter speed, cutter port size, cutter duty cycle, as well as others. Thus, the console 3800 may be operable to control the port size of the example vitrectomy probe 3816. In controlling the vitrectomy port size, a user may indicate a desired port opening size with an input via an input device. For example, the cutter port size may be adjusted via the input device 3808.

In instances in which the vitrectomy probe 3816 includes a piezoelectric motor, such as a piezoelectric motor similar to the piezoelectric motor 926 or 1126 described above, a user may adjust the cutter port size via the input device 3808. In response, the console may output a signal to the piezoelectric motor to effect the desired port size. For example, if an increased port size is indicated, the console 3800 may output an AC current to alter a position of a lead screw thereof to increase the port size. If a decreased port size is indicated, the console 3800 may output an AC current to alter the lead screw position to decrease the port size.

In other instances in which the vitrectomy probe 3816 includes a stroke limiter adjustable by pneumatic pressure, such as the stroke limiters 1460, 1626, 2226, 2626, 3326, or 3926, an input by a user to adjust the port size, such as via input device 3808, causes the console 3800 to alter a pneumatic pressure applied to the probe 3816. For example, in some instances, where a decreased port size is indicated by the user, the console 3800 may increase a pneumatic pressure supplied to the probe 3816. Alternately, where an increased port size is indicated, the console 3800 may respond by decreasing a pneumatic pressure supplied to the probe 3816. In other instances, increased pressure may cause an increase in port size while decreased pressure may cause a decrease in port size. The altered pneumatic pressure is operable to adjust a position of the stroke limiter and, as a result, the port size.

In still other instances, vitrectomy probe 3816 may include a stroke limiter that is altered by an electric device, such as the pancake motor 3526 or motor 3714, described above. The console 3800 may alter the port size of the vitrectomy probe 3816 in response to a user input by altering an electric voltage or current applied to the electrical device.

While examples are provided above, they are provided merely as examples and are not intended to limit the scope of the present disclosure.

In some implementations, the input device 3808 may be a footswitch coupled to the console 3800, such as via a wired or wireless connection. A surgeon may adjust the port size by manipulating a control on the footswitch. For example, the footswitch may include a pedal pivotable within a range, and the surgeon may adjust the port size by actuating the pedal within the range. The footswitch may also include other controls, such as one or more buttons, for example, to adjust a cutting rate (e.g., the rate at which the inner cutting member 130 is reciprocated), an aspiration rate (e.g., an amount of suction applied through the vitrectomy probe), and a duty cycle. Any of these aspects of the vitrectomy probe may be altered independently of the others.

It should be understood that, although many aspects have been described herein, some implementations may include all of the features, while others may include some features while omitting others. That is, various implementations may include one, some, or all of the features described herein.

While one or more of the example probes describes herein are described in the context of pneumatic pressure, the disclosure is not so limiting. Rather, one or more of the probes described herein may be operated, for example, hydraulically or electrically, and the scope of the disclosure is intended to encompass these as well as other manners of operating the probe.

A number of implementations have been described. Nevertheless, it will be understood that various modifications may be made without departing from the spirit and scope of the disclosure. Accordingly, other implementations are within the scope of the following claims.

What is claimed is:

1. A vitrectomy probe comprising:
  a housing;
  a cutter extending from a first end of the housing along a longitudinal axis, the cutter comprising:
    an outer cutting member coupled to the housing;
    an opening formed in the outer cutting member, the opening comprising a distal edge and a proximal edge;
    an interior assembly comprising an inner cutting member slideable within the outer cutting member, the interior assembly slideable between a retracted position and an extended position and comprising a first contact surface; and
    an adjustable port, a size of the adjustable port defined by the distal edge of the opening and an end surface of the inner cutting member when the inner cutting member is in a fully retracted position, the end surface of the inner cutting member being disposed between the distal edge of the opening and the proximal edge of the opening when the inner cutting member is in the fully retracted position;
  an oscillator operable to reciprocate the interior assembly;
  a stroke limiter disposed within the housing, the stroke limiter comprising a second contact surface; and
  a motor operably coupled to the stroke limiter, a position of the stroke limiter relative to the interior assembly being alterable to a plurality of selectable positions in response to a rotation of the motor,
  wherein the first contact surface of the interior assembly contacts the second contact surface of the stroke limiter at a selected position of the plurality of selectable positions to stop motion of the interior assembly and to define the fully retracted position of the inner cutting member.

2. The vitrectomy probe of claim 1, wherein the motor comprises:
  a rotatable shaft; and
  a coupler coupled to the shaft and the stroke limiter.

3. The vitrectomy probe of claim 1, wherein the motor is operable to rotate the stroke limiter about the longitudinal axis.

4. The vitrectomy probe of claim 1, wherein the interior assembly further comprises an extension extending through the oscillator and coupled to the inner cutting member.

5. The vitrectomy probe of claim 4, wherein a location where the stroke limiter contacts the extension defines the fully retracted position.

6. The vitrectomy probe of claim 4 further comprising a passage extending through the interior assembly.

7. The vitrectomy probe of claim 1, wherein the stroke limiter is moveable relative to the housing.

8. The vitrectomy probe of claim 1, wherein the stroke limiter comprises a threaded exterior surface, wherein the housing comprises a threaded bore, and wherein the threaded exterior surface of the stroke limiter matingly engages the threaded bore of the housing.

9. A vitrectomy probe comprising:
  a housing defining an outermost surface of the vitrectomy probe;
  a cutter extending from a first end of the housing along a longitudinal axis, the cutter comprising:
    an outer cutting member attached to a distal end of the housing;
    an interior assembly comprising an inner cutting member slideable within the outer cutting member, the interior assembly slideable between a retracted position and an extended position; and an adjustable port, a size of the adjustable port defined by an edge of an opening formed in the outer cutting member and an end surface of the inner cutting member when the inner cutting member is in a fully retracted position;

an oscillator operable to reciprocate the interior assembly;

a stroke limiter disposed within the housing and operable to limit the size of the adjustable port; and a motor operably coupled to the stroke limiter and operable to displace the stroke limiter along the longitudinal axis relative to the interior assembly, wherein the stroke limiter comprises a first threaded exterior surface, wherein a portion of the housing comprises a second threaded surface, wherein the first threaded surface matingly engages the second threaded surface.

10. The vitrectomy probe of claim 9 further comprising a bore formed in the housing, wherein the second threaded surface is formed on an interior surface of the bore.

11. The vitrectomy probe of claim 9, wherein a rotation of the motor in a first direction displaces the stroke limiter in a first direction along the longitudinal axis and wherein a rotation of the motor in a second direction displaces the stroke limiter in a second direction along the longitudinal axis.

12. The vitrectomy probe of claim 11, wherein displacement of the stroke limiter in the first direction along the longitudinal direction extends the stroke limiter towards the inner cutting member and wherein displacement of the stroke limiter in the second direction along the longitudinal direction retracts the stroke limiter from the inner cutting member.

* * * * *